(12) United States Patent
Ding et al.

(10) Patent No.: US 6,949,644 B2
(45) Date of Patent: Sep. 27, 2005

(54) METHODS FOR THE SYNTHESIS OF SUBSTITUTED PURINES

(75) Inventors: Sheng Ding, San Diego, CA (US); Qiang Ding, San Diego, CA (US); Nathanael S. Gray, San Diego, CA (US); Peter G. Schultz, La Jolla, CA (US)

(73) Assignees: IRM LLC (BM); The Scripps Research Institute, La Jolla, CA (US)

( * ) Notice: Subject to any disclaimer, the term of this patent is extended or adjusted under 35 U.S.C. 154(b) by 52 days.

(21) Appl. No.: 10/270,031

(22) Filed: Oct. 12, 2002

(65) Prior Publication Data

US 2003/0171583 A1 Sep. 11, 2003

Related U.S. Application Data

(60) Provisional application No. 60/348,089, filed on Jan. 10, 2002, provisional application No. 60/347,037, filed on Jan. 8, 2002, provisional application No. 60/346,552, filed on Jan. 7, 2002, provisional application No. 60/346,480, filed on Jan. 7, 2002, provisional application No. 60/331,835, filed on Nov. 20, 2001, provisional application No. 60/328,763, filed on Oct. 12, 2001, and provisional application No. 60/328,741, filed on Oct. 12, 2001.

(51) Int. Cl.[7] .................... C07D 473/16; C07D 473/22; C07D 473/40; C07D 473/18
(52) U.S. Cl. .................. 544/277; 544/264; 544/276; 435/4; 435/DIG. 34
(58) Field of Search ........................................ 544/277

(56) References Cited

U.S. PATENT DOCUMENTS

2003/0176699 A1 * 9/2003 Gray et al. ................. 544/277
2003/0191312 A1 * 10/2003 Ding et al. ................. 544/277

OTHER PUBLICATIONS

Sheng Ding, *Journal of Organic Chemistry* 66, pp. 8273–8276 (2001).*
Kim et al., *J. Med. Chem.*, 43:4126–4134 (2000).
Krchnak et al., *Collect. Czech. Chem. Commun.*, 53:2542–2548 (1988).
Krchnak et al., *Int. J. Pept. Protein Res.*, 32:415–416 (1988).

(Continued)

*Primary Examiner*—Mark L. Berch
(74) *Attorney, Agent, or Firm*—Townsend & Townsend & Crew LLP

(57) ABSTRACT

The invention provides general methods for preparing 2,9-, 2,6,9-, $O^6$-aryl- and $O^6$-alkyl-substituted purines in a combinatorial and traceless fashion. The methods involve, in some embodiments, Mitsunobu alkylation of 2-fluoro-6-phenylsulfenylpurine at N9 with alcohols in solution, followed by C2-capture of the purine core with a resin-bound amine and subsequent oxidation and displacement of the C6 sulfonyl group with amines and anilines. In one aspect, the present invention provides a method of preparing a 2,6,9-substituded purine compounds of Formula I:

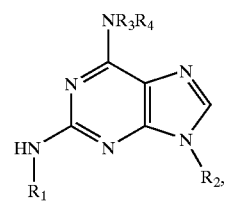

the method comprising:
a) oxidizing a resin-bound compound of Formula II:

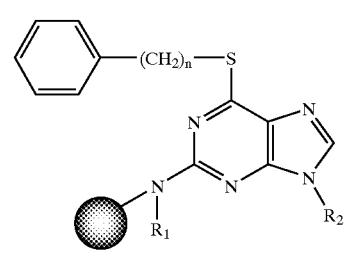

to provide a resin-bound compound of Formula III:

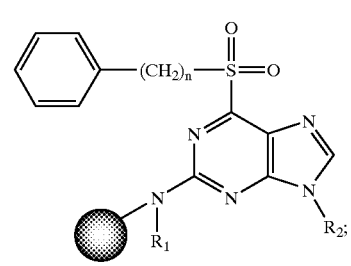

b) reacting the compound of Formula III with an amine of Formula IV

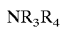

NR$_3$R$_4$     IV, to provide a resin-bound compound of Formula V

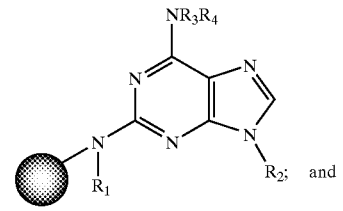

c) cleaving the resin-bound compound of Formula V from the resin to provide the substituted purine compounds of Formula I.

8 Claims, 2 Drawing Sheets

OTHER PUBLICATIONS

Lakshman et al., *Org. Lett.*, 2(7):927–930 (2000).
Lucrezia et al., *J. Comb. Chem.*, 2:249–253 (2000).
McMahon et al., *Current Opinion in Drug Discovery & Development*, 1(2):131–146 (1998).
Nolsoe et al.; *Synth. Commun.*, 28(23):4303–4315 (1998).
Schindler et al., *Science*, 289:1938–1942 (2000).
Taylor et al., *Current Opinion in Chemical Biology*, 1:219–226 (1997).
Tsunoda et al., *Tetrahedron Letters*, 34(10):1639–1642 (1993).
Zaitseva et al., *Bioorganic Med. Lett.*, 5(24):2999–3002 (1995).
Adams et al., *Current Opinion in Drug Discovery & Development*, 2(2):96–109 (1999).
Albericio et al., *J. Org. Chem.*, 55:3730–3743 (1990).
Arris et al., *J. Med. Chem.*, 43:2797–2804 (2000).
Blume–Jensen et al., *Nature*, 411:355–365 (2001).
Boojamra et al., *J. Org. Chem.*, 62:1240–1256 (1997).
Chang et al., *Chemistry and Biology* 6:361–375 (1999).
Cohen, *Current Opinion in Chemical Biology*, 3:459–465 (1999).
Dalby et al., *Angew. Chem. Int. Ed. Engl.*, 32(12):1696–1697 (1993).
Druker et al., *Nature Medicine*, 2(5):561–566 (1996).
Garcia–Echeverria et al., *Med. Res. Rev.*, 20:28–57 (2000).
Gayo et al., *Tetrahedron Lett.*, 38(2):211–214 (1997).
Gray et al., *Science*, 281:533–538 (1998).
Jin et al., *J. Comb. Chem.*, 3:97–101 (2001).

* cited by examiner

METHODS FOR THE SYNTHESIS OF SUBSTITUTED PURINES

CROSS-REFERENCES TO RELATED APPLICATIONS

This patent application claims the benefit of U.S. Provisional Patent Application No. 60/328,741, filed Oct. 12, 2001, U.S. Provisional Patent Application No. 60/346,552, filed Jan. 7, 2002, and U.S. Provisional Patent Application No. 60/347,037, filed Jan. 8, 2002, the teachings of all of which are incorporated herein by reference. This patent application is related to U.S. Provisional Patent Application No. 60/328,763, filed Oct. 12, 2001, U.S. Provisional Patent Application No. 60/331,835, filed Nov. 20, 2001, U.S. Provisional Patent Application No. 60/346,480, filed Jan. 7, 2002, and U.S. Provisional Patent Application No. 60/348,089, filed Jan. 10, 2002, the teaching of all of which are incorporated herein by reference.

BACKGROUND OF THE INVENTION

1. Field of the Invention

This invention pertains to the field of methods for preparing libraries of purine compounds. For example, the invention relates to methods of preparing 2,6,9-substituted purine compounds on solid phase supports by employing sulfenylpurine intermediates. Also provided are methods for preparing 2,9-substituted purines and $O^6$-aryl and $O^6$-alkyl-substituted purines.

2. Background

The sequencing of the human genome and numerous pathogen genomes has resulted in an explosion of new molecular targets that can be modulated by small molecules. Discovering these modulators and further developing them into new therapeutics presents unprecedented opportunities and challenges for academic and industrial researches. One of the most fruitful applications of combinatorial chemistry has been the design of flexible synthetic schemes that generalize a privileged scaffold from a particular target protein to an entire protein family.

Inhibitors of protein kinases have proven to be invaluable tools in the elucidation of signal transduction networks, as well as promising clinical candidates for the treatment of cancer, cardiovascular disease, inflammatory, and neurological diseases. (McMahon et. al., *Current Opinion in Drug Discovery & Development*, 1, 131 (1998); Adams et al., *Current Opinion in Drug Discovery & Development*, 2, 96 (1999); Cohen, P., *Current Opinion in Chemical Biology*, 3, 459 (1999); Garcia-Echeverria et. al., *Med. Res. Rev*, 20, 28 (2000); Blume-Jensen et al., *Nature*, 411, 355 (2001) and references therein) Despite concerns that it would be extremely difficult to design specific ATP competitive inhibitors of kinases, there have been a number of success stories including the p38 Map kinase, tyrosine kinases, and cyclin dependent kinases. (McMahon et. al., *Current Opinion in Drug Discovery & Development*, 1, 131 (1998); Adams et al., *Current Opinion in Drug Discovery & Development*, 2, 96 (1999); Cohen, P., *Current Opinion in Chemical Biology*, 3, 459 (1999); Garcia-Echeverria et. al., *Med. Res. Rev*, 20, 28 (2000); Blume-Jensen et al., *Nature*, 411, 355 (2001) and references therein; Druker et. al., *Nature Medicine*, 2, 561 (1996); Taylor et al., *Current Opinion in Chemical Biology*, 1, 2219 (1997); Schindler et. al., *Science*, 289, 1938 (2000)) Selective inhibitors of each of these kinases are in various stages of clinical testing. The ability to discriminate between extremely homologous kinases such as CDK1 vs. CDK2 has been demonstrated by the development of novel thio-flavopiridol derivatives that display enhanced selectivity for CDK1 relative to CDK2. (Kim et. al., *J. Med. Chem.*, 43, 4126 (2000).)

The purine ring system is a key structural element of the substrates and ligands of many biosynthetic, regulatory and signal transduction proteins including cellular kinases, G proteins and polymerases. In particular, inhibitors of protein kinases have proven to be invaluable tools in the elucidation of signal transduction networks as well as promising clinical candidates in a multitude of disease such as cancer, cardiovascular disease, inflammatory disease and neurological disease. For example, various purine analogs have been found to be highly potent therapeutic agents for disease. As such, the purine ring system has been a good starting point in the search for inhibitors of kinases, G proteins and many biomedically significant processes.

The design of synthetic schemes for generating a multitude of structurally diverse compounds (i.e., library of compounds) typically involves creating the libraries in situ in solution phase or on solid support, i.e., solid phase. In solid phase synthesis, the desired compounds are generated while attached to the solid support via a linker prepared on a polymeric solid support material, e.g., polystyrene.

Several solid phase and solution phase approaches for the synthesis of purine analogs have been reported in the literature over the past five years. (For 2-, 6-, 8- 9-substituted purine analogs, see, e.g., Gray et. al., *Science*, 281, 533 (1998); Chang et. al., *Chemistry and Biology*, 6, 361 (1999); Lucrezia et. al., *J. Comb. Chem.*, 2, 249 (2000); Nolsoe et. al., *Synth. Commun.*, 28, 4303 (1998); for 7-substituted purine analogs, see, e.g., Dalby et. al., *Angew. Chem. Int. Ed. Engl.*, 32, 1696 (1993); Zaitseva et. al., *Bioorganic Med. Lett.*, 5, 2999 (1995).) Unfortunately, these approaches have limitations. One limitation is that one substituent is held invariant in order to anchor the purine ring to the solid phase (Scheme 1). To avoid this limitation, a "traceless" strategy would be desirable that would be compatible with production scale library synthesis in spatially separate or divide-recombine formats.

Scheme 1.
Previously described combinatorial strategies for 2,6,9-trisubstituted purines

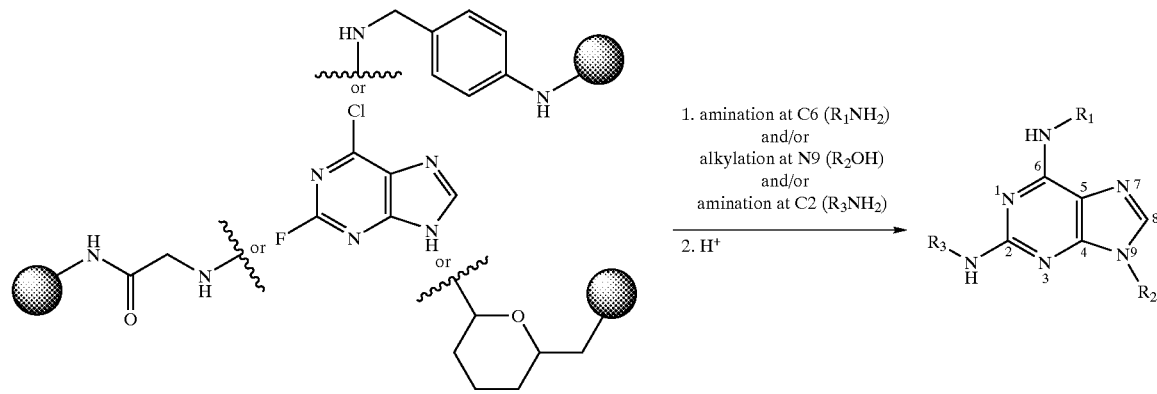

Another limitation of previous synthetic approaches is the low reactivity of the 2-fluoro group once an amino substituent has been installed at C6. For example, complete displacement at C2 of a 2-fluoro-6-benzylaminopurine in solution requires heating at over 100° C. for twelve hours using n-butanol as solvent. Complete aromatic substitution of 2-fluoro or 2-chloro purine compounds on solid support requires even higher temperatures and often results in significant side reactions. This limits the range of functional groups that can be installed at C2 and also creates difficulties in library production.

Subsequently, it was found that 6-amino-2-fluoro-9-alkylpurines react with primary amines in methanol at room temperature. With slightly more forcing conditions (in refluxing methanol) sterically hindered amines such as the alpha-amino group of arginine could be successfully introduced at the C2 position (Scheme 2) with good yields. Unfortunately, these conditions failed to translate to solid support, presumably due to resin swelling problems in methanol. Despite testing a range of solvent systems (NMP, DMF, dioxane, DMSO, THF and their combinations such as $DMF^v/MeOH^v:1/1$), no solvent was found that allowed complete substitution below 100° C.

Scheme 2.
Couple amino acids to purine C2 position

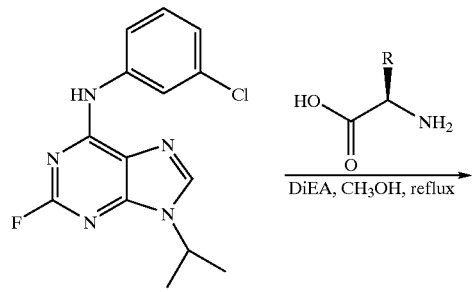

-continued

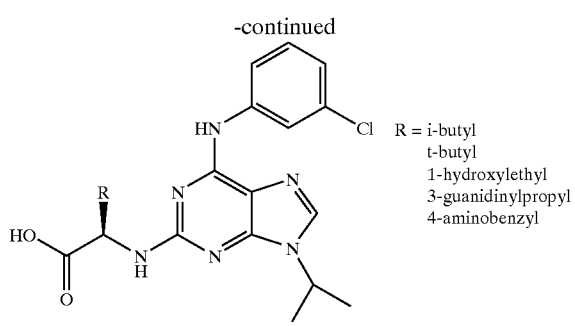

R = i-butyl
t-butyl
1-hydroxylethyl
3-guanidinylpropyl
4-aminobenzyl

Since a number of purine compounds have been shown to possess diverse pharmacological properties and biological activities in a number of therapeutic areas, the generation of a substituted purine compound library would be useful as a screening tool to identify the structures of compounds that possess the desired biological activity. In addition, the generation of substituted purine library would permit alteration of the structures of the identified compounds to identify derivatives of these compounds which exhibit the best biological activity and which also have ideal pharmacological and pharmacokinetic properties. Accordingly, the development of an efficient, rapid in situ method for the generation of a multitude of highly substituted purine compounds that would overcome limitations of known procedures would be highly desirable.

Moreover, to date a variety of heterocyclic scaffolds including pyrimidines, indolines, pyrrolopyrimidines, indirubins, purines, quinazolines, trisubstituted imidazoles, pyrazolopyrimidines, have been developed as kinase inhibitors. ((a) McMahon et. al., *Current Opinion in Drug Discovery & Development*, 1, 131 (1998); (b) Adams et al., *Current Opinion in Drug Discovery & Development*, 2, 96 (1999); (c) Cohen, P., *Current Opinion in Chemical Biology*, 3, 459 (1999); (d) Garcia-Echeverria et. al., *Med. Res. Rev*, 20, 28 (2000); (e) Blume-Jensen et al., *Nature*, 411, 355 (2001) and references therein; (f) Druker et. al., *Nature Medicine*, 2, 561 (1996); (g) Taylor et al., *Current Opinion in Chemical Biology*, 1, 2219 (1997); (h) Schindler et. al., *Science*, 289, 1938 (2000).) As each scaffold presents unique opportunities for the presentation of functional groups to the kinase active site, there is a need for efficient and flexible methods for preparing libraries of each of these inhibitor classes. The present invention fulfills these and other needs.

SUMMARY OF THE INVENTION

The present invention is directed to methods of preparing diverse 2,6-, 2,9, 2,6,9-, $O^6$-alkyl- and $O^6$-aryl-substituted purine compounds on solid support phase. In some embodiments, the methods involve using a novel intermediate compound, a 2-halo-6-sulfenyl purine. The invention also encompasses these sulfenylpurine intermediates and methods for their preparation.

As such, in one aspect, the present invention provides a method of preparing a 2,6,9-substituted purine compounds having the Formula I:

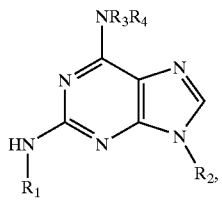

I the method comprising:

a) oxidizing a resin-bound compound of Formula II:

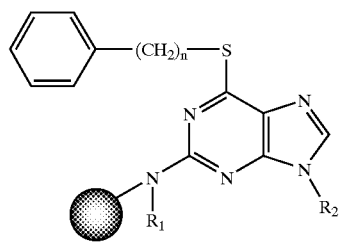

II to provide a resin-bound compound of Formula III:

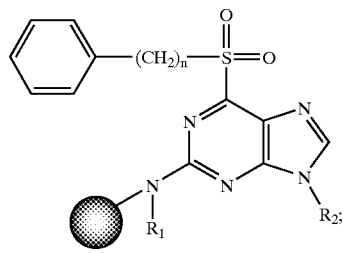

III b) reacting the compound of Formula III with an amine of Formula IV

NR₃R₄

IV, to provide a resin-bound compound of Formula V

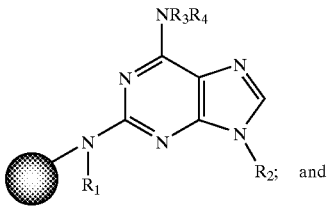

V and c) cleaving the resin-bound compound of Formula V from the resin to provide the substituted purine compounds of Formula I.

In Formula I, $R_1$ and $R_2$ are independently selected and are functional groups including, but not limited to, alkyl, substituted alkyl, cycloalkyl, aryl, substituted aryl, arylalkyl, substituted arylalkyl and heterocyclyl; $R_3$ is hydrogen; and $R_4$ is a functional group including, but not limited to, alkyl, substituted alkyl, cycloalkyl, aryl, substituted aryl, arylalkyl, substituted arylalkyl and heterocyclyl; or, $R_3$ and $R_4$ when taken together with the nitrogen and carbon atoms to which they are respectively attached form an optionally substituted saturated heterocyclic ring.

In Formulae II and III, $R_1$ and $R_2$ are as defined above and n is 0 or 1. In Formula IV, $R_3$ and $R_4$ are as defined above. In Formula V, $R_1$, $R_2$, $R_3$ and $R_4$ are as defined above.

In a preferred embodiment, the compound is a compound of Formula II, and can be prepared using a method comprising:

a) alkylating a compound of Formula VI:

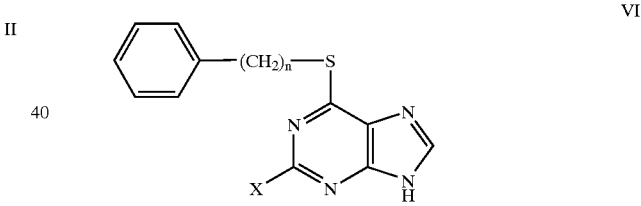

VI to provide a compound of Formula VII:

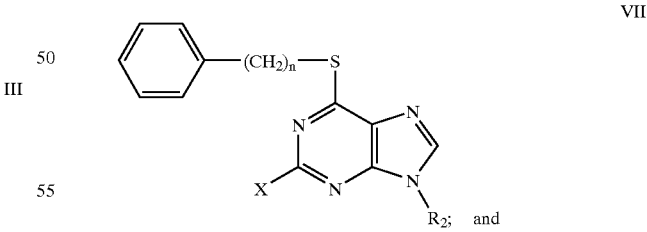

VII and b) capturing the compound of Formula VII with a resin-bound amine to provide the resin-bound compound of Formula II.

In the above method, X, in Formula VI, is fluoro, chloro or bromo, and n is as defined above. In Formula VII, $R_2$, X and n are as defined above.

In another preferred embodiment, the compound of Formula II can be prepared using a method comprising:

a) capturing a compound of Formula VI

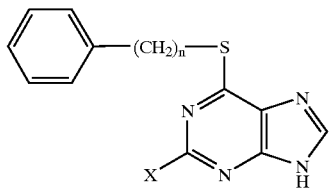

VI with a resin-bound amine to provide a resin-bound compound of Formula VIII:

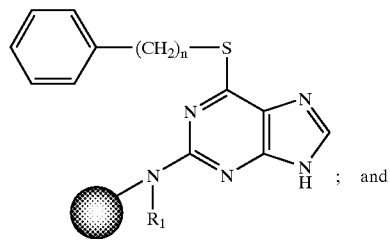

VIII

; and b) alkylating the resin-bound compound of Formula VIII to provide the resin-bound compound of Formula II.

In Formula VI, X and n are as defined above. In Formula VII, $R_1$ and n are as defined above.

In a preferred embodiment, the compound of Formula VI is prepared by reacting 2-halo-6-halo-purine with a compound of Formula IX:

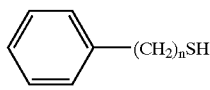

IX to provide the compound of Formula VI, wherein n is as defined above. In a preferred embodiment, the halo groups of the 2-halo-6-halo-purine compound are fluoro, chloro, bromo or iodo and, preferably chloro.

In a preferred embodiment of the above method, step (a) is carried out with m-chloroperbenzoic acid in a buffered solution. In a preferred embodiment of the above method, step (c) is carried out in the presence of trifluoroacetic acid. In a preferred embodiment, alkylation of the compound of Formula VI is carried out in the presence of an inert solvent and a phosphine (e.g., triphenylphosphine, tricyclohexylphosphine, etc.). In a preferred embodiment, the resin is 4-formyl-3,5-dimethyloxyphenoxymethyl functional polystyrene resin.

The present invention also provides a combinatorial library or array comprising a plurality of 2,6,9-substituted purine compounds prepared by the above method.

In another aspect, the present invention provides a compound of Formula VI:

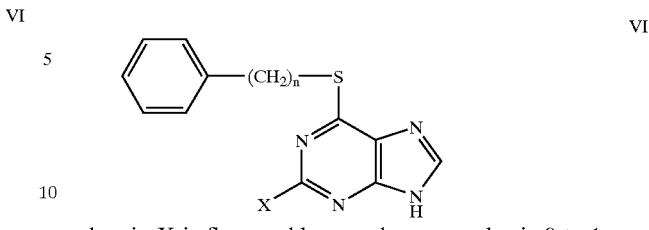

VI wherein X is fluoro, chloro, or bromo, and n is 0 to 1.

In another aspect, the present invention provides a method of preparing 2,9-substituted purine compounds having the Formula X:

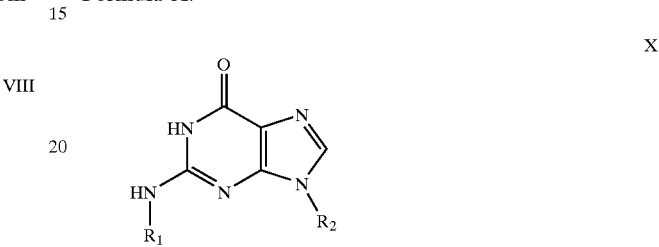

X the method comprising:
a) oxidizing a resin-bound compound of Formula II

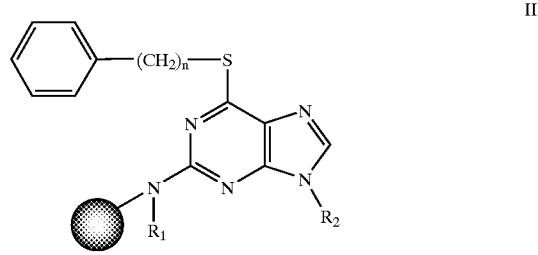

II to provide a resin-bound compound of Formula III

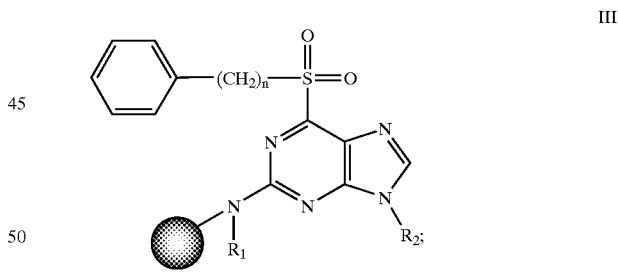

III b) hydrolyzing the sulfonyl group at the 6-position of the resin-bound compound of Formula III; and cleaving the hydrolyzed resin-bound compound from the resin to provide the substituted purine compounds of Formula X In the above method, $R_1$ and $R_2$ are independently selected and are functional groups including, but not limited to, alkyl, substituted alkyl, cycloalkyl, aryl, substituted aryl, arylalkyl, substituted arylalkyl and heterocyclyl; and n is 0 or 1.

In the above method for 2,9-substituted purine compounds, the resin-bound compound of Formula II is prepared using one of the methods set forth above for preparing such compound.

The present invention also provides a combinatorial library or array comprising a plurality of 2,9-substituted purine compounds prepared by the above method.

In another aspect, the present invention provides a method for preparing O⁶-alkyl-purine compounds of Formula XI:

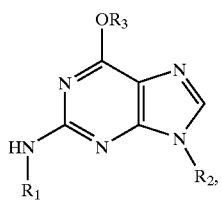

XI the method comprising:

a) oxidizing a resin-bound compound of Formula II

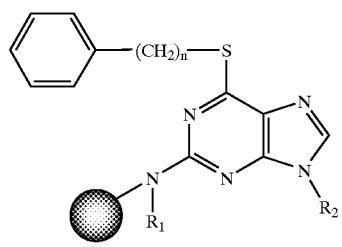

II to provide a resin-bound compound of Formula III

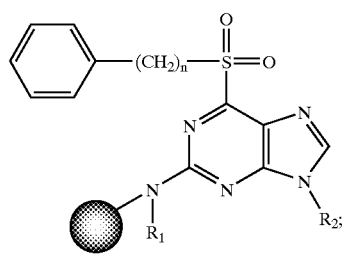

III b) hydrolyzing the sulfonyl group at the 6-position of the resin-bound compound of Formula III to form a resin-bound compound of Formula XII

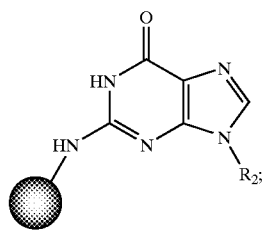

XII c) alkylating the resin-bound compound of Formula XII and cleaving the resin-bound alkylated compound from the resin to provide a compound of Formula XI In the above method, $R_1$ and $R_2$ are independently selected and are functional groups including, but not limited to, alkyl, substituted alkyl, cycloalkyl, aryl, substituted aryl, arylalkyl, substituted arylalkyl and heterocyclyl; $R_3$ is a functional group including, but not limited to, alkyl and substituted alkyl; and n is 0 or 1.

In the above method for preparing O⁶-alkyl-purine compounds, the resin-bound compound of Formula II is prepared using one of the methods set forth above for preparing such compound.

The present invention also provides a combinatorial library or array comprising a plurality of O⁶-alkyl-purine compounds prepared by the above method.

In another aspect, the present invention provides a method for preparing O⁶-aryl purine compounds of Formula XIII:

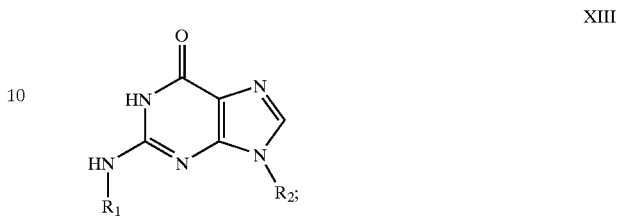

XIII the method comprising:

a) oxidizing a resin-bound compound of Formula II

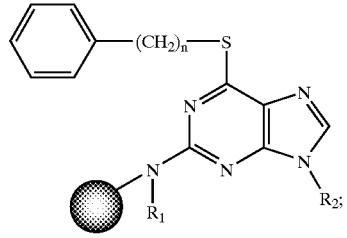

II to provide a resin-bound compound of Formula III

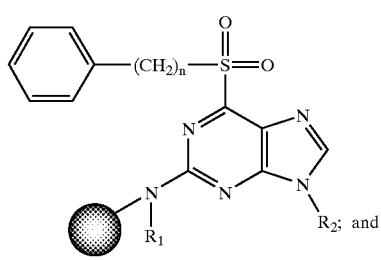

III b) reacting the resin-bound compound of Formula III with an aryl compound (such as a phenolic compound) followed by cleavage of the resin-bound compound to provide a compound of Formula XIII In the above method, $R_1$ and $R_2$ are independently selected and are functional groups including, but not limited to, alkyl, substituted alkyl, cycloalkyl, aryl, substituted aryl, arylalkyl, substituted arylalkyl and heterocyclyl; $R_3$ is a functional group including, but not limited to, aryl or substituted aryl; and n is 0 or 1.

In the above method for preparing O⁶-aryl-purine compounds, the resin-bound compound of Formula II is prepared using one of the methods set forth above for preparing such compound.

The present invention also provides a combinatorial library or array comprising a plurality of O⁶-aryl-purine compounds prepared by the above method.

In another aspect, the present invention provides a method for preparing a compound of Formula VI:

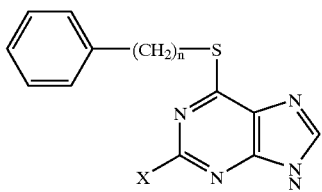

the method comprising:
reacting a 2-halo-6-chloro-purine with a compound of Formula IX

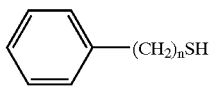

to provide the compound of Formula VI.

In the above method, X is fluoro, chloro or bromo; and n is 0 or 1.

In another embodiment, the present invention provides a method for the for synthesis of a C2-substituted purine, the method comprising reacting a C6-sulfenylpurine with a nucleophile, wherein X is halogen, and the nucleophile is substituted at the C2 position of the purine. In one embodiment, the nucleophile is an amine. In another embodiment, the C6-sulfenylpurine comprises a solid support, Formula XIV:

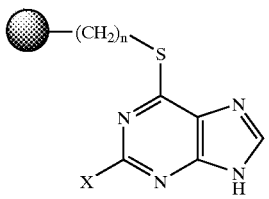

wherein X is a halogen. In another embodiment, the method further comprises oxidizing a thioether linkage between the purine and the sulfenyl moiety to a sulfone of Formula XV:

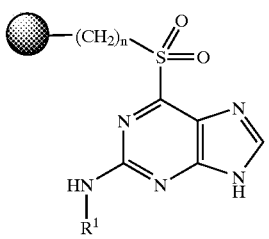

wherein $R^1$ is a functional group including, but not limited to, alkyl, substituted alkyl, cycloalkyl, aryl, substituted aryl, arylalkyl, substituted arylalkyl and heterocyclyl, and substituting a different group at the C6 position of the purine. In a preferred embodiment, the C6 sulfenylpurine is a 2-fluoro-6-phenylsulfenyl or a 2-fluoro-6-benzylsulfenyl.

Other features, objects and advantages of the invention and its preferred embodiments will become apparent from the detailed description which follows.

DETAILED DESCRIPTION OF THE INVENTION AND PREFERRED EMBODIMENTS

Definitions

Figure 1:
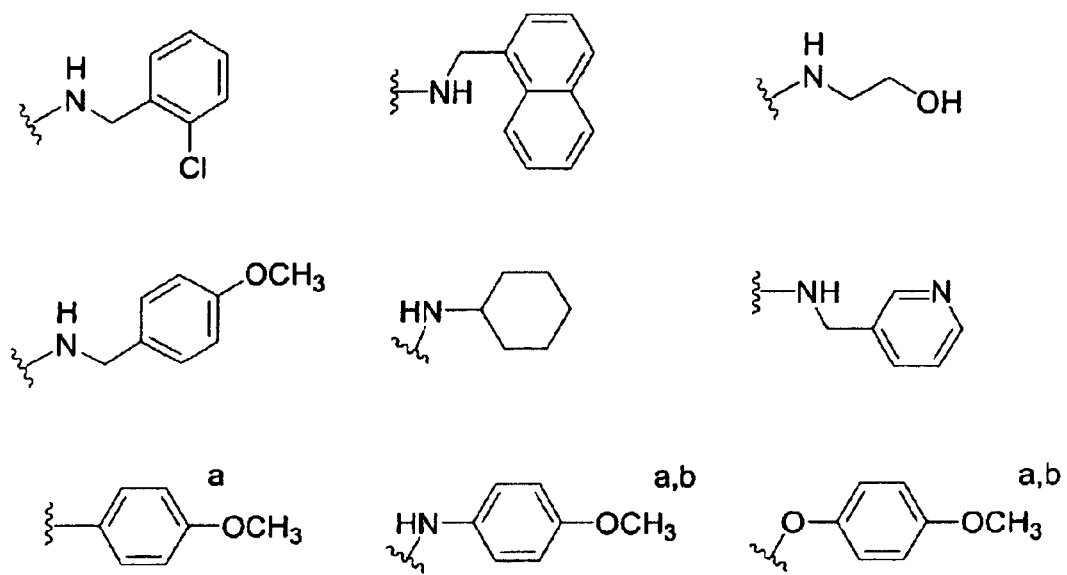
FIG. 1 shows examples of substituents that have been introduced at the C2 position of purines using the methods of the invention as shown in Scheme 6. These substituents were introduced by palladium catalyzed cross-coupling reactions using $Pd_2(dba)_3$, carbene or phosphine ligand, corresponding boronic acid and $Cs_2CO_3$ for C—C bond formation, aniline and KO$^t$Bu for C—N bond formation, phenol and $K_3PO_4$ for C—O bond formation. These substituents can also be introduced by reacting with corresponding aniline/phenol and KO$^t$Bu in THF at 70° C.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used herein, the term "leaving group" refers to a portion of a substrate that is cleaved from the substrate in a reaction.

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., *Protective Groups In Organic Synthesis*, John Wiley & Sons, New York (1991).

The term "alkyl," by itself or as part of another substituent, means, unless otherwise stated, a straight or branched chain hydrocarbon radical, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like.

The terms "alkenyl" and "alkynyl" refer to unsaturated hydrocarbon groups having one or more double bonds or triple bonds, respectively. Examples of suitable unsaturated hydrocarbon groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2S(O)_2$—$CH_3$, —CH=CH—O—$CH_3$, —Si$(CH_3)_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si$(CH_3)_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo $(C_1-C_4)$alkyl" is mean to include trifluoromethyl, 2,2,2-trifluoroethyl, 4-chlorobutyl, 3-bromopropyl, and the like.

The term "aryl" means, unless otherwise stated, an aromatic, hydrocarbon substituent, which can be a single ring or multiple rings (up to three rings), which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidy 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR"R', —NR"C(O)R', —NR'—C(O)NR"R'", —NR"C(O)$_2$R', —NR—C(NR'R")=NR'", —S(O)R', —S(O)$_2$R', —S(O)$_2$ NR'R", —NRSO$_2$R', —CN and —NO$_2$, —R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R", R'" and R"" are preferably independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl)oxy-(C$_1$–C$_4$)alkyl. When a compound of the invention includes more than one R group, for example, each of the R groups is independently selected as are each R', R", R'" and R"" groups when more than one of these groups is present.

The term "independently selected" is used herein to indicate that the R groups, e.g., R1 and R2, can be identical or different (e.g., R.1 and R2 may all be substituted alkyls or R1 may be a substituted alkyl and R2 may be an aryl, etc.). A named R group will generally have the structure which is recognized in the art as corresponding to R groups having that name. For the purposes of illustration, representative R groups as enumerated above are defined herein. These definitions are intended to supplement and illustrate, not preclude, the definitions known to those of skill in the art.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR''' R''')$_d$—, where s and d are independently integers of from 0 to 3, and X is —O—, —NR'—, —S—, —S(O)—, —S(O)$_2$—, or —S(O)$_2$NR'—. The substituents R, R', R'' and R''' are preferably independently selected from hydrogen or substituted or unsubstituted (C$_1$-C$_6$)alkyl.

As used herein, the term "heterocycle," refers to both heterocycloalkyl and heteroaryl groups.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66, 1–19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Description of the Preferred Embodiments

The present invention provides solid phase methods of preparing diverse purine compounds. For example, the present invention provides methods for producing 2,6-, 2,6,9-, 2,9-, O$^6$-alkyl-, and O$^6$ aryl-substituted purine compounds as well as novel substituted purine compounds. In some embodiments, the methods use novel C-6 sulfenylpurine compounds as intermediates. Methods of preparing the intermediates are also encompassed by the present invention.

The methods of the present invention overcome limitations described above in preparing 2,6 and 2,6,9-substituted purines by, for example, employing 1) an arylsulfenyl group as a "protective" group at the C6 position of the purine ring which when subsequently oxidized to an arylsulfonyl group allows the quantitative and selective substitution by an amine to the C2 position prior to substitution at the C6 position; and 2) in preferred embodiments, a "traceless" amine linkage to solid support, wherein the amine linker is incorporated into the final purine compound.

The methods described herein are useful not only for substitution of purines, but also of other heterocycles. For example, the methods are suitable for use with a combinatorial scaffold approach towards heterocycle libraries, as described in U.S. Provisional Patent Application No. 60/331,835, which is entitled "Kinase Inhibitor Scaffolds," and which was filed on Nov. 20, 2001, in U.S. Provisional Patent Application No. 60/346,480, which is entitled "Kinase Inhibitor Scaffolds," and which was filed on Jan. 7, 2002, and in U.S. Provisional Patent Application No. 60/348,089, which is entitled "Kinase Inhibitor Scaffolds," and which was filed on Jan. 10, 2002. The methods are also suitable for use in conjunction with the methods described in U.S. Provisional Patent Application No. 60/328,763, which is entitled "Expanding the Diversity of Purine Libraries," and which was filed on Oct. 12, 2001.

Preparation of 2,6,9-Substituted Purines

Accordingly, in one aspect, the present invention provides a method of preparing a 2,6,9-substituted purine compounds having the Formula I

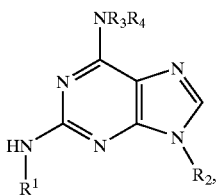

the method comprising:
a) oxidizing a resin-bound compound of Formula II:

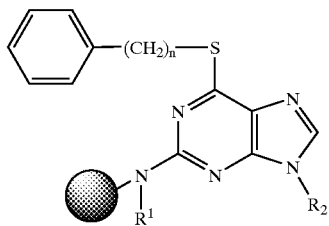

to provide a resin-bound compound of Formula III:

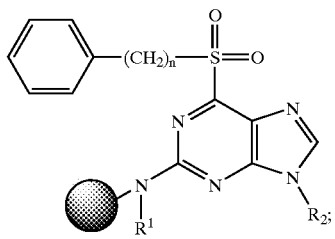

b) reacting the compound of Formula III with an amine of Formula IV

to provide a resin-bound compound of Formula V

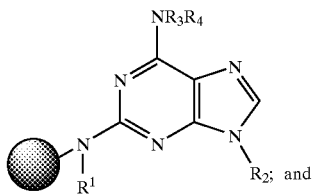

c) cleaving the resin-bound compound of Formula V from the resin to provide the substituted purine compounds of Formula I.

In Formula I, $R_1$ and $R_2$ are independently selected and are functional groups including, but not limited to, alkyl, substituted alkyl, cycloalkyl, aryl, substituted aryl, arylalkyl, substituted arylalkyl and heterocyclyl; $R_3$ is hydrogen; and $R_4$ is a functional group including, but not limited to, alkyl, substituted alkyl, cycloalkyl, aryl, substituted aryl, arylalkyl, substituted arylalkyl and heterocyclyl; or, $R_3$ and $R_4$ when taken together with the nitrogen and carbon atoms to which they are respectively attached form an optionally substituted saturated heterocyclic ring.

In Formulae II and III, $R_1$ and $R_2$ are as defined above and n is 0 or 1. In Formula IV, $R_3$ and $R_4$ are as defined above. In Formula V, $R_1$, $R_2$, $R_3$ and $R_4$ are as defined above.

The resin utilized to bind the compound of Formula II in step (a) refers to a polymeric resin, including, but not limited to, polystyrene, polypropylene, polyethylene glycol, polyacrylamide, cellulose and the like which has been chemically modified by an amino group as is described in more detail below. The amino group is eventually incorporated into the purine compound as described in more detail below.

Oxidation of the resin-bound compound of Formula II is generally carried out at room temperature utilizing a suitable oxidizing reagent and a solvent. Suitable oxidizing agents include, but not limited to, perbenzoic acid, m-chloroperbenzoic acid, performic acid, peracetic acid, perphthalic acid, and the like. Preferably, the oxidizing agent is m-chloroperbenzoic acid. Suitable solvents include, but are not limited to, water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

Preferably, the reaction is also carried out in the presence of a base to neutralize the oxidizing agent, thereby providing a buffered solution. Suitable bases include, but are not limited to, inorganic bases such as alkali metal hydroxides, e.g., sodium hydroxide, potassium hydroxide, etc., and alkaline earth metal hydroxides such as magnesium hydroxide and calcium hydroxide. In a typical protocol, a solution comprising an oxidizing agent and a solvent is cooled down to about 0° C., followed by the addition of NaOH and the resin-bound compound of Formula II. The suspension is then shaken or mixed at room temperature, and the resultant resin-bound oxidized compound of Formula III is then washed with a solvent, such as methanol and dichloromethane, and dried under vacuum.

The amine employed in step (b) to displace the sulfone group of the compound of Formula III includes, but is not limited to, primary amines, cyclic secondary amines (such as piperazines) and electron-rich anilines (see, e.g., Table 1-"C6-substituent" column). The reaction is conveniently effected by suspending the compound of Formula III in an inert solvent, such as 1,4-dioxane, followed by the addition of the amine. The resin-bound compound is then washed in a solvent such as methanol and dichloromethane, and dried under vacuum to provide the resin-bound compound of Formula V.

Cleavage of the resin-bound compound of Formula V and liberation of the desired compound of Formula I from the resin as described in step (c) of the method is typically carried in the presence of an acid. Suitable acids include, but are not limited to, an organic acid such as formic acid, acetic acid, propionic acid, trichloroacetic acid, trifluoroacetic acid and the like, and inorganic acids such as hydrochloric acid, hydrobromic acid, sulfuric acid, hydrogen chloride, etc., or the like. The reaction is usually carried out in a solvent such as water, an alcohol such as methanol, ethanol, 1,4, dioxane, methylene chloride, tetrahydrofuran, a mixture thereof or any other solvent which does not adversely influence the reaction.

Once the desired purine compound is freed from the resin by cleavage, it can be isolated by simply removing the solvent, e.g., by filtration.

In a preferred embodiment, the compound is a compound of Formula II, and can be prepared using a method comprising:

a) alkylating a compound of Formula VI:

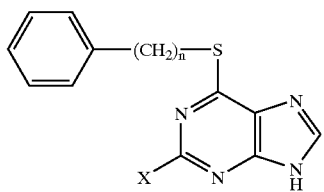
VI to provide a compound of Formula VII:

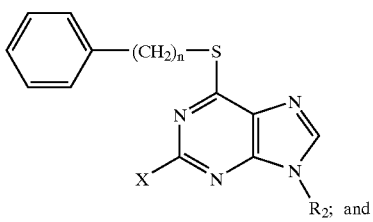
VII

R₂; and b) capturing the compound of Formula VII with a resin-bound amine to provide the resin-bound compound of Formula II.

In the above method, X, in Formula VI, is fluoro, chloro or bromo, and n is as defined above. In Formula VII, R₂, X and n are as defined above.

Alkylation of the N9 position of the compound of Formula VI as described in step (a) of preparing the compound of Formula II can be effected under known conditions, e.g., Mitsunobu conditions as described, e.g., in Tsunoda et al., *Tetrahedron Letters*, 34, 1639 (1993). In a typical Mitsunobu reaction, the compound of Formula VI is mixed with an alcohol, e.g., a primary, secondary or tertiary alcohol, in approximately equimolar amounts or with an excess of either compound, in an inert solvent, such as tetrahydrofuran, chloroform or dichloromethane. A slight molar excess of an azodicarboxylate, e.g., diisopropyl azodicarboxylate, and a phosphine, e.g., triphenylphosphine or tributylphosphine, are added, and the reaction is stirred at a temperature, e.g., room temperature, for a sufficient amount of time to obtain the compound of Formula VII.

Alternatively, the compound of Formula II can be prepared using a method comprising:

a) capturing a compound of Formula VI

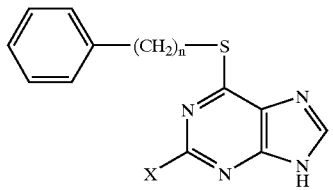
VI with a resin-bound amine to provide a resin-bound compound of Formula VIII:

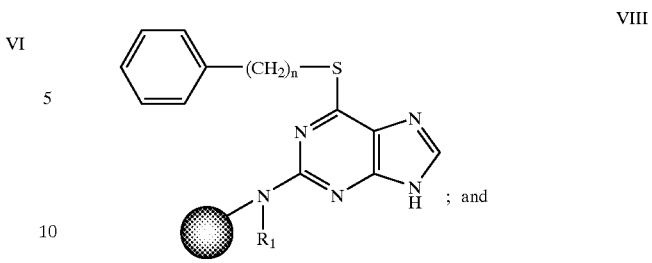
VIII

; and b) alkylating the resin-bound compound of Formula VIII to provide the resin-bound compound of Formula II.

In Formula VI, X and n are as defined above. In Formula VII, R₁ and n are as defined above.

In order to adapt the methods set forth above so that they are useful in a combinatorial scheme, the C6 position can be substituted following oxidation of the thioether to the sulfone, as demonstrated in the synthesis of 2,4-diaminopyridine (Gayo et al., *Tetrahedron Lett.*, 38, 211 (1997)). The 2-fluoro-6-thiophenylpurine can be prepared by reacting excess thiophenol with 2-fluoro-6-chloropurine in methanol at 0° C. and purified by recrystallization.

Scheme 3.
Sulfenyl group protecting purine C6 position

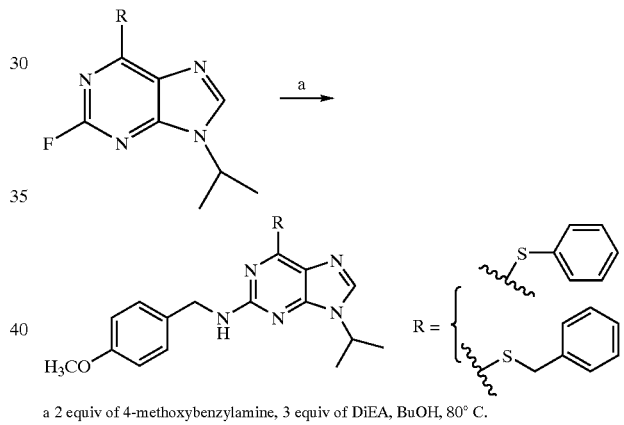

a 2 equiv of 4-methoxybenzylamine, 3 equiv of DiEA, BuOH, 80° C.

It has previously been demonstrated that the N9 position can be alkylated on a solid support under Mitsunobu conditions with a variety of alcohols. However, performing the N9-modification reaction on a solid support had several drawbacks including incomplete alkylation with secondary alcohols, consumption of large excesses of reagent, and inconvenient handling of reaction in a 96-well format. To circumvent this problem, a method has now been developed, whereby a resin-bound amine is used to capture a C6-phenylsulfenyl-N-9-alkylpurine directly from the crude reaction mixture. This allows the moisture sensitive Mitsunobu reaction to be performed as the first combinatorial step in solution making the overall scheme more convergent.

To achieve a "traceless" linkage to solid support, primary amines are coupled by reductive amination using, e.g., sodium triacetoxyborohydride to a 4-formyl-3,5-dimethoxyphenoxymethyl functionalized polystyrene resin (PAL). (Albericio et. al., *J. Org. Chem.*, 55, 3730 (1990); Boojamra et. al., *J. Org. Chem.*, 62, 1240 (1997); Jin et. al., *J. Comb. Chem.*, 3, 97 (2001).) The purine ring can then, for example, be captured at the C2-position by reacting the PAL-amine resin with 1.5 equivalents of the crude N9-alkylated 2-fluoro-6-phenylsulfenylpurine and 3 equivalents of di-isopropylethylamine in n-butanol at 80° C. The C6 position can then be substituted following oxidation-activation of the thioether to the sulfone (see, Scheme 2). The use of m-chloroperbenzoic acid to oxidize the thioether linkage can result in the premature cleavage from solid support presumably as a result of acid and oxidant sensitivity of the benzylic PAL-amine linkage. This problem can be overcome, for example, by performing the oxidation in buffered solution with m-chloroperbenzoic acid that had been neutralized with a stoichiometric amount of sodium hydroxide.

This combinatorial scheme of the present invention has the following merits: (1) the difficulty of C2 substitution is overcome by "directing" the first substitution to C2 by using phenylsulfenyl group as a "protective" group at the C6 position; (2) N9 modification is accomplished in solution and purified by resin-capture; (3) the PAL linker allows traceless cleavage; and (4) construction of focused C6 purine libraries can readily be accomplished because this is the last step in the combinatorial synthesis scheme. As such, the method of the present invention has numerous advantages over any previously used method.

The scope of the chemistry has been validated for a wide range of substituents. Most primary and secondary alcohols lacking additional acidic hydrogens work well in the Mitsunobu reaction at N9 (see, Table 1). As the Mitsunobu reaction is performed on the C6-phenylsulfenylpurine, there is very little detectable contamination from the N7 regioisomer. Alkylation can also be performed with active alkylbromides (such as t-butyl-bromoacetate) or N9 can be temporally protected with, for example, the THP group to provide additional diversity. C2 substituents are preferably limited to primary amines (e.g., Table 1) due to the need for a reaction site to attach the purine to solid support. In some embodiments, it has been found that immobilized anilines only result in partial capture of the purine from solution. Because m-chloroperbenzoic acid is used in preferred embodiments to convert the C6 thioether to a sulfone in the final activation step, substituents having functional groups prone to oxidation cannot be readily used in the first two derivatization steps. C6 displacement of the sulfone works for primary amines, cyclic secondary amines (such as piperazines) and electron-rich anilines (see, Table 1).

Scheme 4.
Traceless combinatorial approach toward 2,6,9-trisubstituted purine library

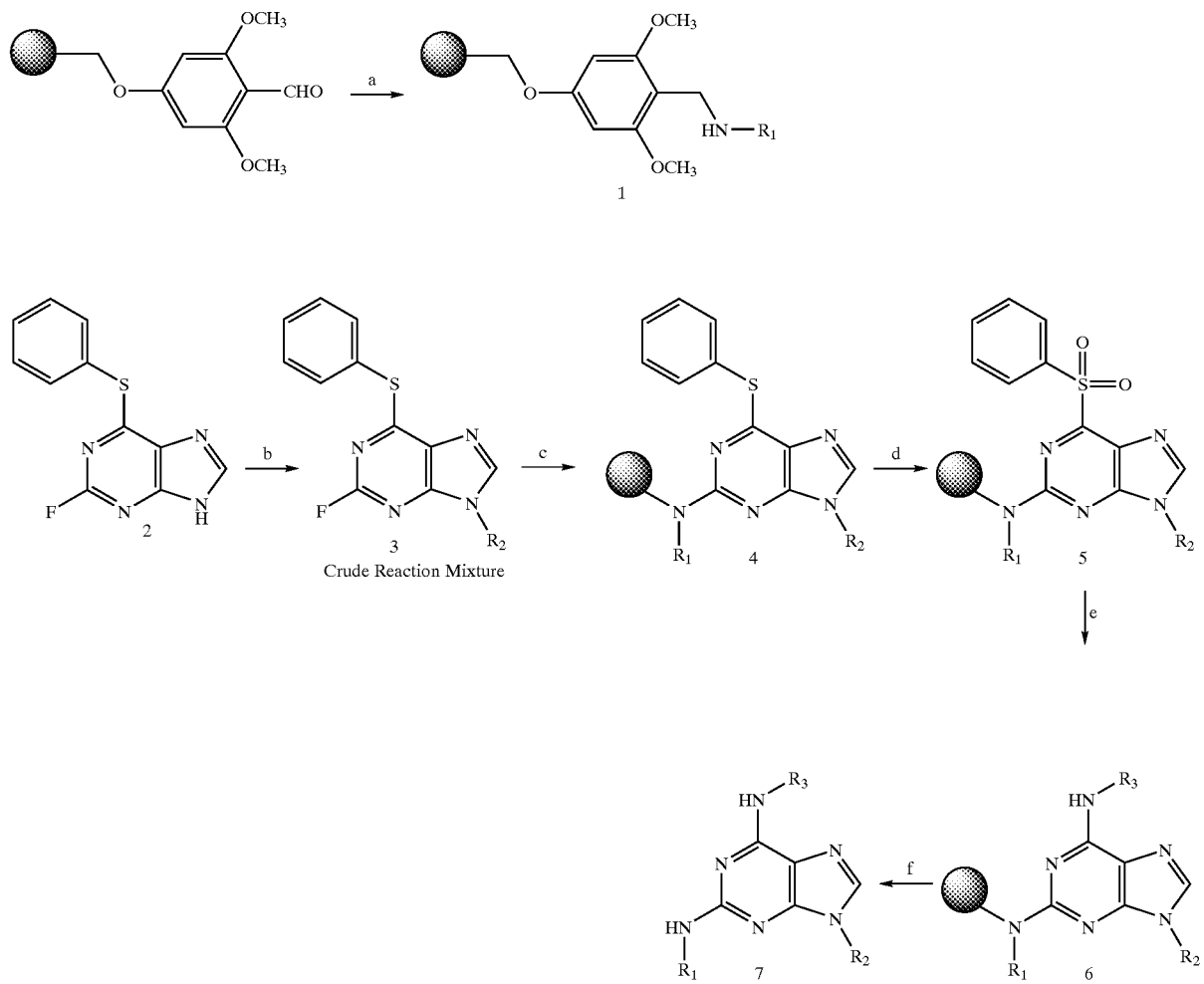

a. 5 equiv of R$_1$-NH$_2$, 3 equiv of NaBH(OAc)$_3$, 1% HOAc, THF; b. 1.5 equiv of R$_2$OH, 1.8 equiv of PPh$_3$, 1.3 equiv of DiAD, THF, RT; c. 0.5 equiv of 1, 1.5 equiv DiEA, BuOH, 80° C.: d. 10 equiv of m-CPBA/NaOH (1:1), 1,4-dioxane with 10% H$_2$O; e. 2equiv of R$_3$-NH$_2$, anhydrous dioxane, 80° C.; f. CH$_2$Cl$_2$: TFA:Me$_2$S:H$_2$O/45:45:5:5

TABLE 1

N-9 substituent (R$_2$) introduced by alkylation; C-2 substituent (R1) introduced through resin-bound amines; C-6 substituent (R$_3$) introduced by displacement with amines

| N9 substituent (R$_2$) | C2 substituent (R$_1$) | C6 substituent (R$_3$) |
|---|---|---|

TABLE 1-continued

N-9 substituent (R₂) introduced by alkylation; C-2 substituent (R1) introduced through resin-bound amines; C-6 substituent (R₃) introduced by displacement with amines

| N9 substituent (R₂) | C2 substituent (R₁) | C6 substituent (R₃) |
|---|---|---|
| 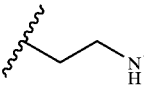 a | 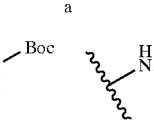 | 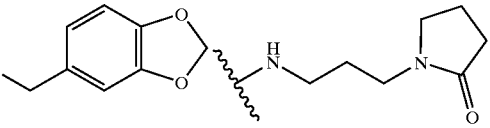 |
| 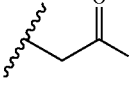 b | 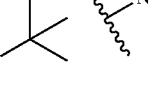 | 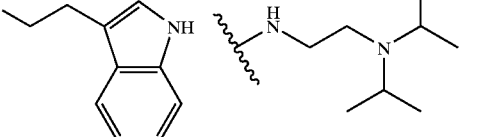 |
| 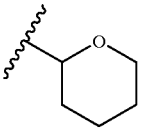 c | 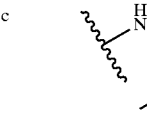 | 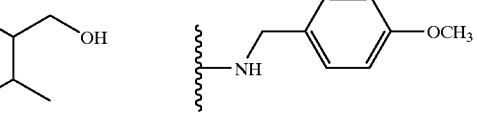 |

Except c, which was made by reacting purine with 3 equiv of DHP, cat. PPTS, and b, which was made by alkylation with 3 equiv of t-bytyl-bromoacetate all other substituents (R₂) were introduced by Mitsunobu alkylation. It should be noted that after final TFA cleavage, a, b and c gave arise to corresponding deprected forms.

In summary, the methods of the present invention provide a concise and traceless linker strategy that is extremely useful for preparing 2,6,9-trisubstituted combinatorial purine libraries. Resin-bound amines are used to capture a C6-phenylmecapto-9-alkylated purine directly from the crude Mitsunobu alkylation reaction mixture. The C6 position is then substituted following oxidation-activation of the thioether to the sulfone. This strategy overcomes the difficulty of C2 substitution by "directing" the first substitution to C2 by using a phenylsulfenyl group to protect the C6 position. A thousand compound combinatorial purine library has been synthesized using this approach in 96-well format. Detailed procedures, and results showing the validation of the methods for synthesis of substituted purines having a wide variety of different substituents are shown in Example 1.

It will be readily apparent that the foregoing discussions regarding oxidizing agents, solvents, bases, alkylating agents and resins as well as the foregoing discussions regarding the capturing step, the alkylating step, the cleaving step, the purification step, etc. are fully applicable to all of the methods disclosed and claimed herein, including the preferred embodiments.

Preparation of 2,9-Disubstituted and O⁶-aryl- and O⁶-alkyl-substituted Purines

Screening purine libraries has resulted in the identification of diverse molecules that inhibit mitosis, alter cellular morphology, and induce apoptosis. The guanine ring also serves as a key recognition determinant in biological systems and guanine derivatives have been developed as GTPase and phosphodiesterase inhibitors as well as antiviral agents. This aspect of the invention provides diverse solid phase approaches useful for the synthesis of combinatorial guanine and other purine libraries.

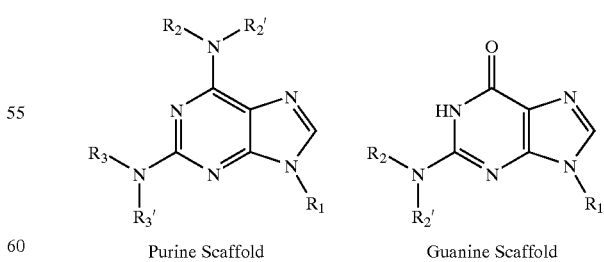

Purine Scaffold      Guanine Scaffold

Initially, the synthesize 2,9-disubstituted guanines was attempted by Mitsunobu alkylation of 2-bromohypoxanthine in solution with an alcohol followed by nucleophilic modification of C2 by a resin-bound amine (see, Scheme 5)

Scheme 5.
2,9-Disubstituted guanines from protected 2-bromohypoxanthine

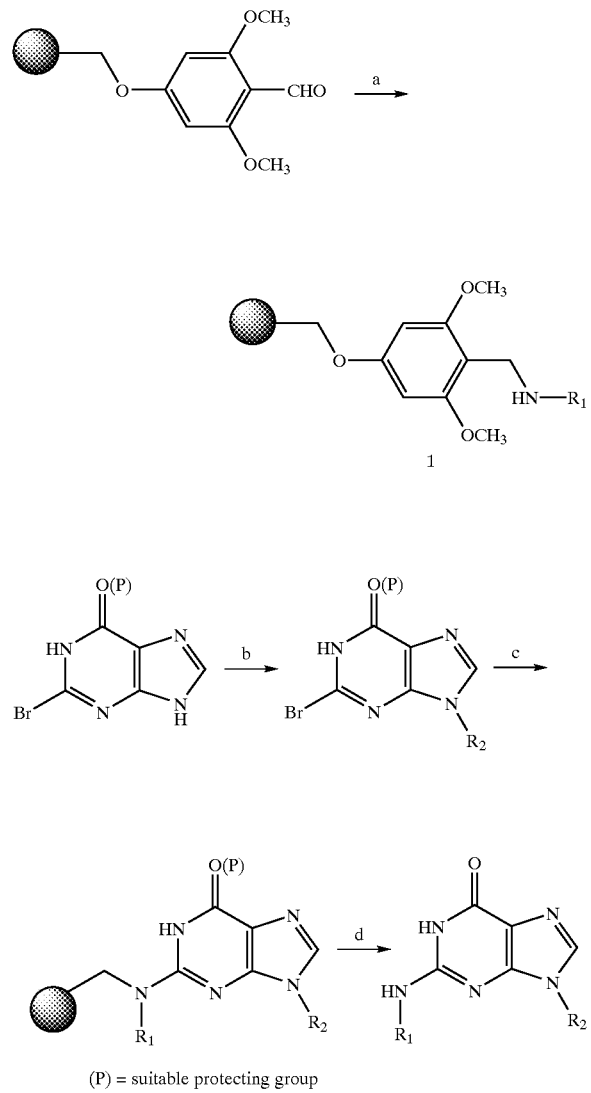

(P) = suitable protecting group a. R$_1$—NH$_2$, NaBH(OAc)$_3$, 1% HOAc, THF, b R$_2$OH, PPh$_3$, DiAD, THF, c 1, DiEA, BuOH, 80° C., d CH$_2$Cl$_2$ TFA Me$_2$S H$_2$O/45 5:5

Unfortunately, alkylation under Mitsunobu conditions resulted in a mixture of the N9/C6 regioisomers presumably resulting from the presence of the C6 phenol tautomer. Instead of exploring approaches that involve cumbersome protecting group manipulation at C6 and N9 positions, reaction conditions were determined that would discriminate between these positions. This was accomplished, for example, by capturing an N9-alkylated 2,6-dichloropurine onto Wang resin, which serves as both linker and a protective group for phenol, followed by functionalization of C2 by amination or palladium catalyzed cross-coupling chemistry (see, Scheme 6). Modification of N9 was achieved by regioselective alkylation of 2,6-dichloropurine under Mitsunobu conditions as previously reported. The purified N9-alkylpurine could be captured onto Wang resin by treatment with 1.2 equivalents of potassium t-butoxide in THF for 8 hours. The quantitative C2 amination was accomplished with non-hindered primary and secondary amines at 100° C. in DMSO for 12 hours. In order to derivatize the C2 position with anilines, palladium-catalyzed cross-coupling conditions were required to drive the reaction to completion. The typical conditions involved reaction of the 2-chloropurine substrate with 5 equivalents of aniline in the presence of Pd$_2$(dba)$_3$ (7 mol %), carbene ligand 1 (14 mol %), and 6 equivalents of KO$^t$Bu in anhydrous 1,4-dioxane under argon. The reactions are typically complete after stirring at 80° C. for 12 hours. Under similar palladium catalyzed coupling condition, the 2-chloro can be reacted with arylboronic acids to form direct C—C bond connections and with phenols to form C—O connections. Although the reaction time and the amount of coupling reagents used could be optimized for each type of reaction and substrate, the general coupling protocol described above was found to be most general for achieving quantitative conversion of the starting material (the chloro-group at the C2 position of purine) with different substrates on the solid support. This approach is ideally suited for focusing diversity at the C2 position of guanine. With R$_1$ fixed as isopropyl (which can be readily modified with a variety of alcohols by Mitsunobu alkylation), a variety of substituents (R$_2$) have been introduced into the C2 position (see, FIG. 1).

Scheme 6

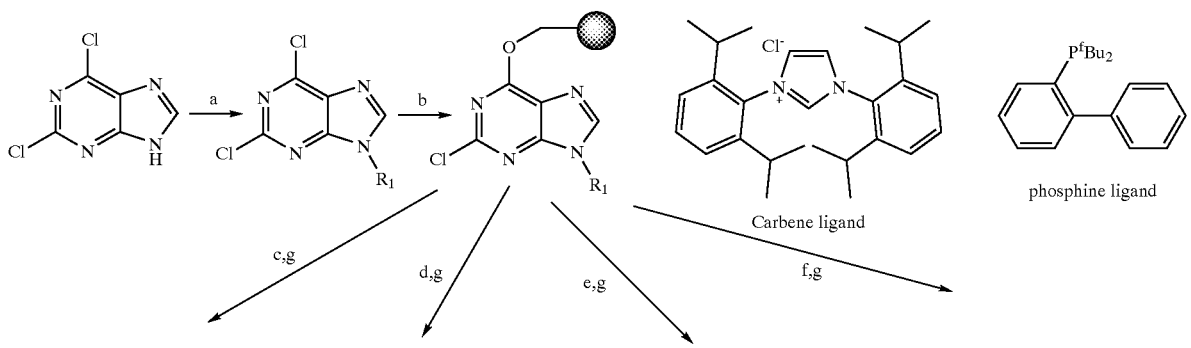

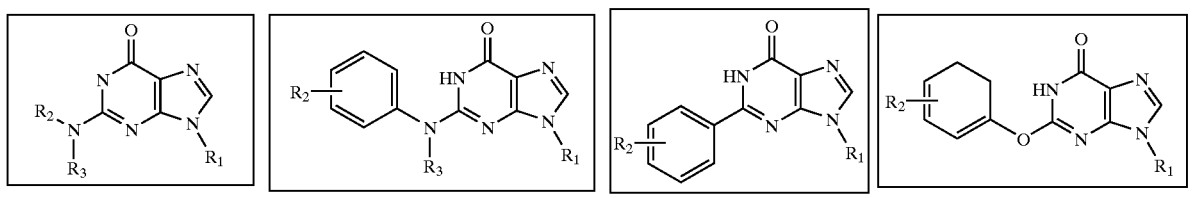

a. R₁OH, PPh₃, DiAD, THF: b. Wang resin, KO^tBu, THF, 0° C.; c. 5 equiv of R₂R₃NH, 7.5 equiv of DiEA, DMSO, 100° C.; d. 5 equiv of anilines, 7% of Pd₂(dba)₃, 14% of carbene ligand, 6 equiv of KO^tBu, dioxanes, 80° C.; e. 5 equiv of boronic acids, 7% of Pd₂(dba)₃, 14% of carbene ligand, 6 equiv of Cs₂CO₃, dioxanes, 80° C.; f. 5 equiv of phenols, 7% of Pd₂(dba)₃, 28% of phosphine ligand, 7 equiv of K₃PO₄, toluene, 80° C.; g. CH₂Cl₂:TFA:Me₂S:H₂O/45:45:5:5

In addition to the foregoing method, which is described in U.S. Provisional Patent Application No. 60/328,763, filed Oct. 12, 2001, U.S. Provisional Patent Application No. 60/331,835, filed Nov. 20, 2001, U.S. Provisional Patent Application No. 60/346,480, filed Jan. 7, 2002, U.S. Provisional Patent Application No. 60/348,089, filed Jan. 10, 2002, and U.S. patent application Ser. No. 10/270,030, filed on Oct. 12, 2002, the teaching of all of which are incorporated herein by reference, the present invention provides an alternative method in which a 6-phenylmercaptopurine is alkylated at N9, followed by capture at C2 with a resin-bound amine and subsequently converted to the guanine derivative by oxidation of the sulfenyl group to sulfonyl group and its subsequent hydrolysis (Scheme 7). This scheme has also been developed to prepare 2,6,9-trisubstituted purines.

Scheme 7

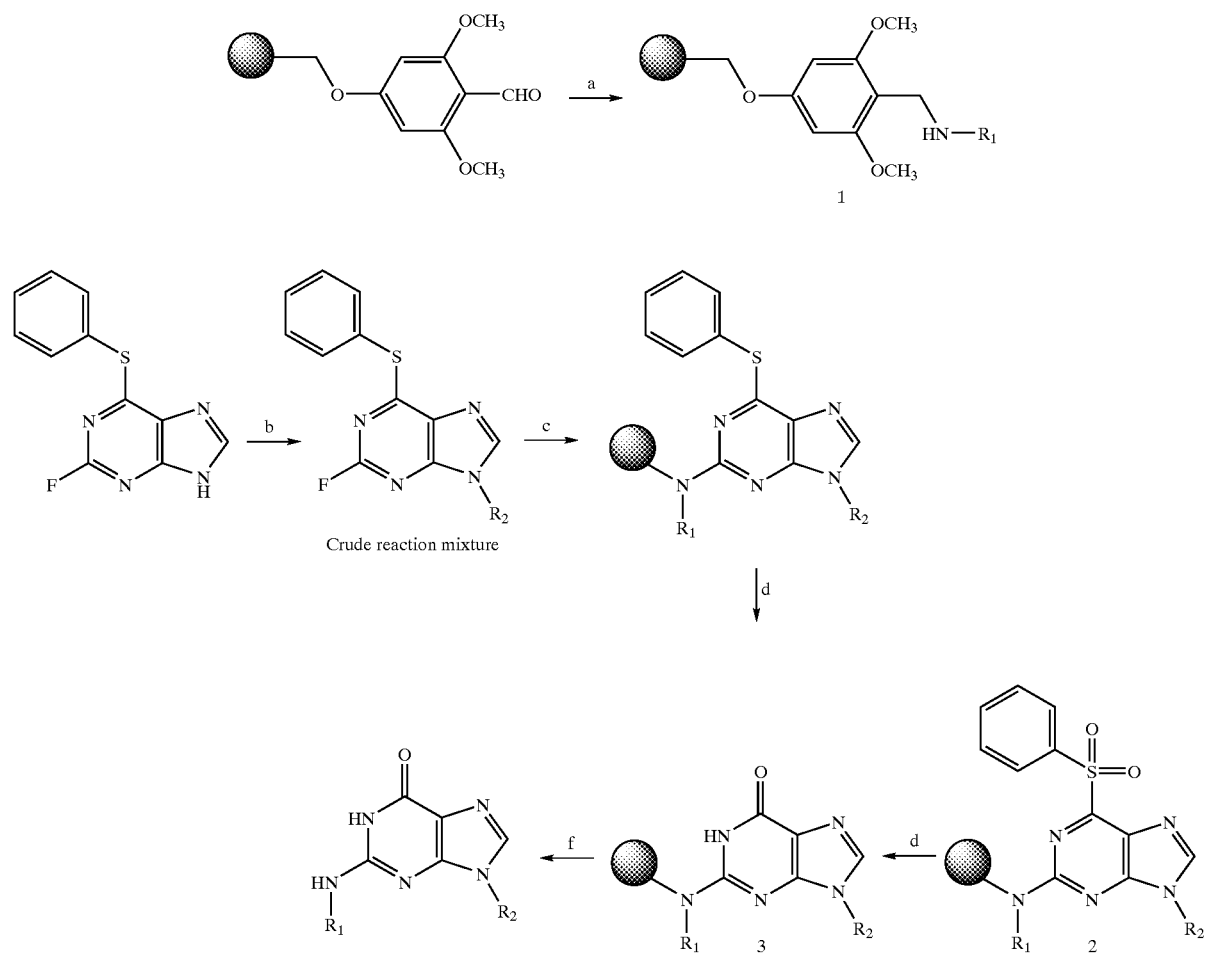

a. R₁—NH₂, NaBH(OAc)₃, 1% HOAc, THF; b. 1.5 equiv of R₂OH, 2 equiv of PPh₃, 1.3 equiv of DiAD, THF, RT; c. 0.5 equiv of 1, 1.5 equiv DiEA, BuOH, 80° C. d. 10 equiv of m-CPBA/NaOH(1:1), 1,4-dioxane with 10% H₂O; e. 5 equiv of NaOH, 1,4-dioxane with 10% H₂O, 80° C.; f. CH₂Cl₂:TFA:Me₂S:H₂O/45:45:5:5

The Wang resin capture strategy allows focused diversity at the C2 position with versatile reactions such as palladium catalyzed cross-coupling reactions, but requires purification of the Mitsunobu product in the first step and high temperatures for chloride displacement conditions. The second approach offers the opportunity of focusing diversity at the N9 position without the need for purification of the Mitsunobu product and effects the C2 functionalization under mild conditions, but limits the C2 substituents to primary amines.

In another aspect, the present invention provides methods to synthesize $O^6$-aryl- and $O^6$-alkyl-purines, which are closely related to guanine analogs and have exhibited interesting biological activities. For example, $O^6$-cyclohexylmethylguanine has been shown to be a competitive inhibitor of cyclin-dependent kinase 1 and 2 (CDK1 and 2) and exhibits an unique binding mode to the ATP-binding site (see, Arris et. al., *J. Med. Chem.*, 43, 2797 (2000)). Resin-bound guanine 3 (from scheme 7) offers direct access to $O^6$-alkyl-purines by Mitsunobu alkylation. Alternatively, resin-bound 6-benzenesolfonylpurine 2 could serve as a versatile intermediate to $O^6$-aryl-, $O^6$-alkyl-purines through DABCO/DBU mediated SNAR displacement reaction (Scheme 8). As shown in Table 2, a variety of phenols were validated using the methods of the present invention and all of them gave satisfactory results.

Scheme 8

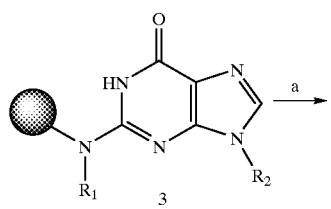

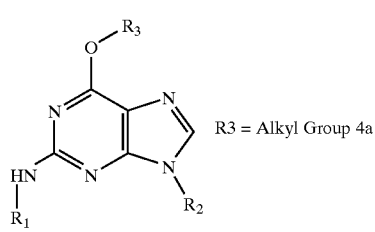

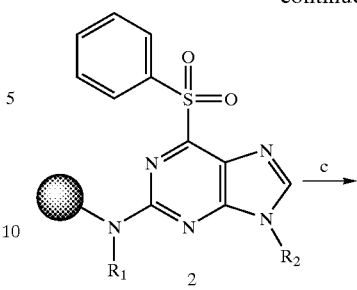

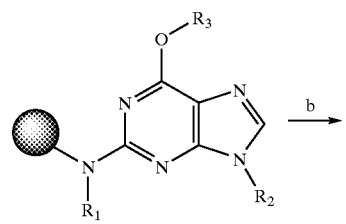

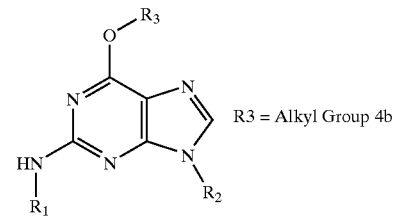

a. $R_3OH$, $PPh_3$, DiAD, THF; b. $CH_2Cl_2$: TFA:$Me_2S$:$H_2O$/45:5:5 c. DABCO, DBU, $R_3$—OH, molecular sieves, 1,2-DME, 60° C.

When alcohols were used as substrates for displacing the benzenesulfonyl group (resin 2), only the guanine analog was obtained presumably as a result of hydrolysis. To circumvent this problem, the use of a more active sulfonate leaving group was explored, which had been demonstrated displaced by alcohols successfully in solution phase. (Lakshman et. al., *Org. Lett.*, 2, 927 (2000).) To adapt this chemistry to solid phase, 2-bromohypoxanthine was loaded on PAL-amine resin at C2 position without protection of the N9. After activation of the C6 position by reaction with mesitylenesulfonyl chloride, a variety of phenols and alcohols can be coupled to the purine (Scheme 9), providing a more general route to $O^6$-aryl-, $O^6$-alkyl-purines (Table 2).

Scheme 9

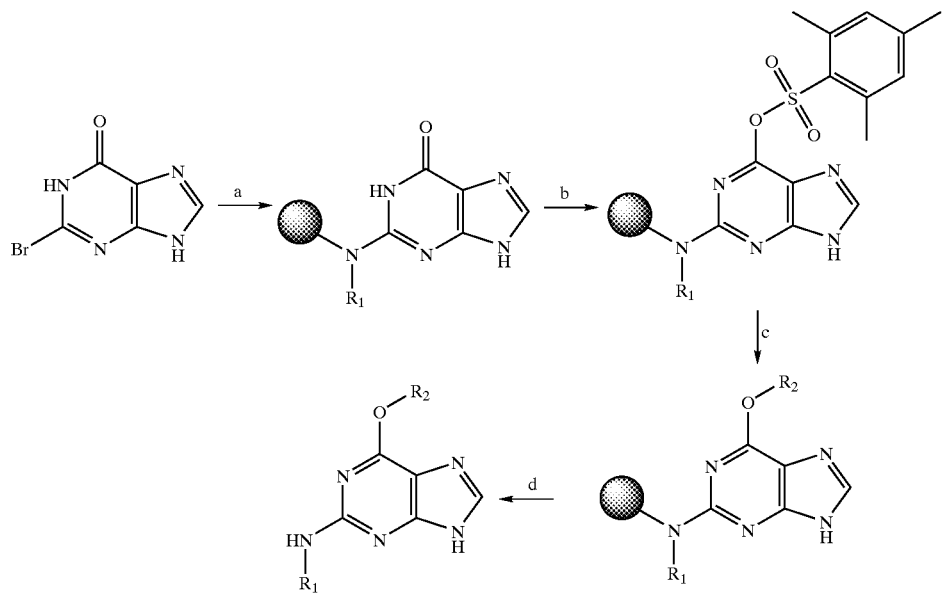

a. 1, DiEA, BuOH, 80° C.; b. TsCl, DMAP; c. DABCO, DBU, R$_2$—OH, molecular sieves, 1,2-DME, 60° C.; d. CH$_2$Cl$_2$:TFA:Me$_2$S:H$_2$O/45:45:5:5

In summary, the methods of the present invention provide general and versatile solid phase strategies for the synthesis of combinatorial guanine and O$^6$-aryl- and O$^6$-alkyl-purine libraries. 2,9-Disubstituted guanine analogs and O-aryl/alkyl purine analogs can be constructed from commercially available purine or hypoxanthine in a traceless fashion, thus allowing ease access to compound libraries.

TABLE 2

| Entry | C6 substituent (OR) | Purity (%) |
|---|---|---|
| | 2-methyl-4-iodophenoxy | 83 |
| | 3-(trifluoromethoxy)phenoxy | 87 |
| | 4-cyclopentylphenoxy | 86 |
| | 7-methoxy-2-naphthyloxy | 86 |
| | 4-methoxyphenoxy | 90 |

TABLE 2-continued

| Entry | C6 substituent (OR) | Purity (%) |
|---|---|---|
| | 2-methyl-5-isopropylphenoxy | 83 |
| | 3-biphenyloxy | 87 |
| | 5-indanyloxy | 90 |
| | 1-naphthyloxy | 89 |
| | 4-(n-hexyloxy)phenoxy | 82 |

TABLE 2-continued

| Entry | C6 substituent (OR) | Purity (%) |
|---|---|---|
| | 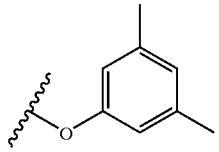 | 87 |
| | 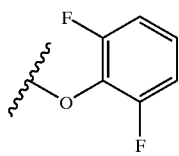 | 82 |
| | 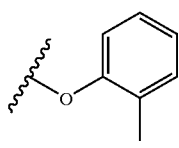 | 83 |
| | 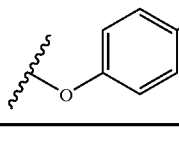 | 84 | above in which a 6-phenylsulfenylpurine scaffold was captured at the C2 position with a resin-bound amine (see also, Sheng and Gray, U.S. Provisional Patent Appl. No. 60/328,741, entitled "A Concise and Traceless Linker Strategy Towards Combinatorial Libraries of 2,6,9-substituted Purines," which was filed on Oct. 12, 2001). The C2 capture approach, which is shown in Scheme 4, is ideally suited for the traceless synthesis of focused C6-purine libraries. However, it has two limitations for some applications: (1) because the C2 amino substitutent is tethered to the solid support prior to being covalently attached to the scaffold, only primary amines can be installed at the C2 position; and (2) it is inefficient to prepare C2 focused libraries as this substitution reaction is the first combinatorial step. To address and overcome these limitations, the present invention provides a complementary approach in which resin capture can be performed at the C6 position, resulting in a resin-bound purine that can be derivatized in a final step at C2.

It is known that the 2-sulfonyl group of 4-aminosubstituted pyrimidines can be displaced by various amines (see, Gayo et al., *Tetrahedron Lett.*, 38, 211 (1997)). Because 2,4-dichloropyrimidine has similar amination reactivity as 2,6-dichloropurines under basic conditions (the 4 position of pyrimidine and the 6 position of purines undergo selective nucleophilic substitution first; complete substitution of the 2 position afterward requires elevated temperature and high concentrations of amine nucleophile), the same can be true for the purine system. Accordingly, the synthetic approach shown in scheme 10 was devised.

Scheme 10.
C2 sulfone group cannot be displaced by amines

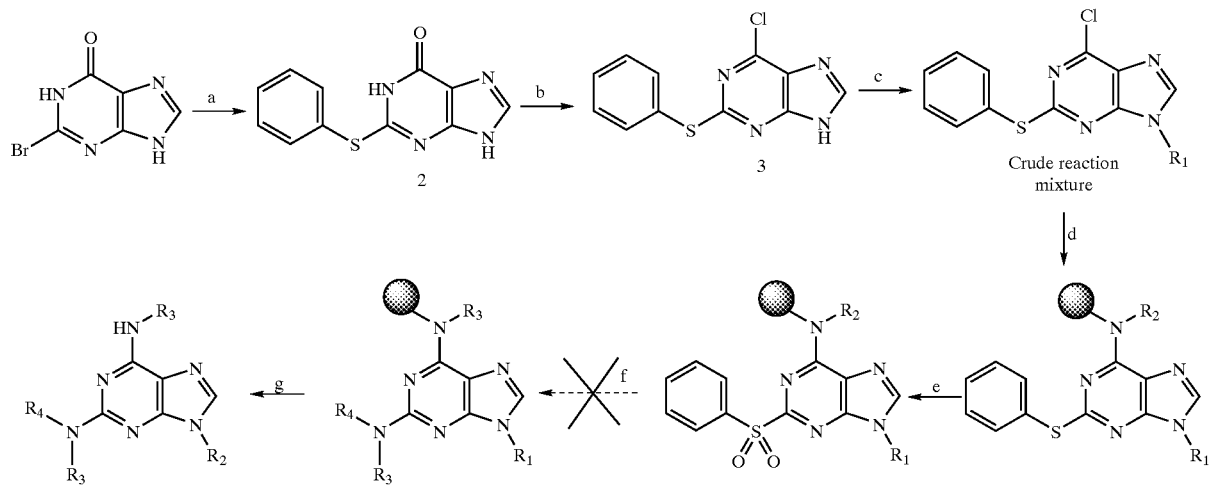

a). 2 equiv of thiophenol, 3 equiv of DiEA, MeOH, 80° C.: b). 6 equ iv of POCl$_3$, 2 equiv of Bu$_4$NCl, 1 equiv of N,N-dimethlaniline, anhydrous CH$_3$CN, reflux; c). 1.5 equiv of R$_1$OH, 1.8 equiv of PPh$_3$, 1.3 equiv of DiAD, THF, RT; d). 0.5 equiv of 1, BuOH, 1 equiv of DiEA , 80° C.; g). CH$_2$Cl$_2$:TFA:Me$_2$S:H$_2$O/45:45:5:5

Resin-Capture-Release Method for Preparation of 2,6,9-Substituted Purines

In another aspect, the present invention provides a resin-capture-release strategy for making combinatorial 2,6,9-trisubstituted purine libraries by capturing N9 derivatized purines at the C6 position with a thio-modified polymer. The C2 halo (e.g., fluoro) group is subsequently substituted with primary and secondary amines, followed by thioether oxidation and release by C6 substitution with amines and anilines. This approach complements the strategy discussed The starting scaffold, 2-thiophenyl-6-chloropurine, can be obtained by thiophenol displacement of commercially available 2-bromohypoxanthine followed by chlorination with POCl$_3$ in 90% overall yield. Mitsunobu reaction can first be used to carry out alkylation reactions at the N9 position. Resin-bound amine 1, which is obtained by reductive amination of a 4-formyl-3,5-dimethoxyphenoxymethyl functionalized polystyrene resin (PAL), is used to capture the N9 alkylated purine from the crude Mitsunobu reaction mixture by nucleophilic substitution at C6. Unfortunately, C2 oxidation to the sulfone and subsequent displacement with amines under a variety of conditions resulted in only the 2-phenylsulfonyl-6-aminosubstituted purine product, consistent with the observation that nucleophilic displacement of C2 on a C6 amino-substituted purine is difficult.

To avoid substitution at the C6 position with an amine prior to derivatization of the C2 position, the present invention provides a method in which the purine is first linked to solid support at the C6 via a thioether. The thioether linked purine is obtained by resin-capture of the crude N9 Mitsunobu alkylation product at C6 using a methylmercapto resin. The C2 position is subsequently derivatized by a nucleophilic substitution reaction with amines. The C6 substituent is then introduced by displacement of the sulfonyl group with amines after oxidative activation of thioether linkage and the final product is released into the reaction solution (Scheme 11). This approach offers, inter alia, the following advantages: (1) secondary amines can be introduced at the C2 position; (2) only the activated polymer-bound purine intermediate can be released; (3) the activated sulfone linker allows traceless cleavage; and (4) construction of focused C2 purine libraries can readily be accomplished by coupling different amines at the C2, and using a single amine for the final displacement. As such, this method of the present invention provides an advantage relative to scheme 4 due to the technical difficulty in preparing Pal-amine resins by reductive amination in an array format.

This method of the present invention has been validated for a broad range of substituents on the purine ring. Most primary and secondary alcohols lacking additional acidic hydrogens work well in the N9 Mitsunobu reaction (as described herein). Quantitative alkylation of the starting purine can be achieved by using excess alkylating reagent (1.5 equivalents of alcohol, 1.6 equivalents of diisopropyl azodicarboxylate and 2.0 equivalents of triphenylphosphine). The Mitsunobu alkylation step can also be performed on solid support after the resin-capture of 2-fluoro-6-chloropurine. This procedure resulted in very small quantities of the minor N7 Mitsunobu regioisomer, but required considerably more alkylating reagents.

Scheme 11.
Resin-capture-release strategy towards
combinatorial libraries of 2,6,9-trisubstituted purines

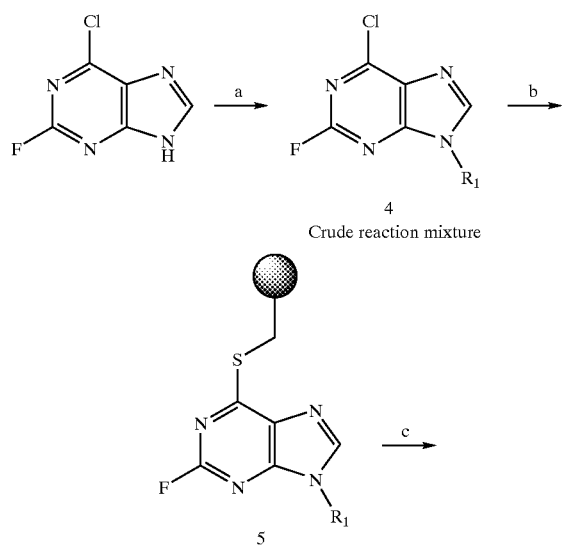

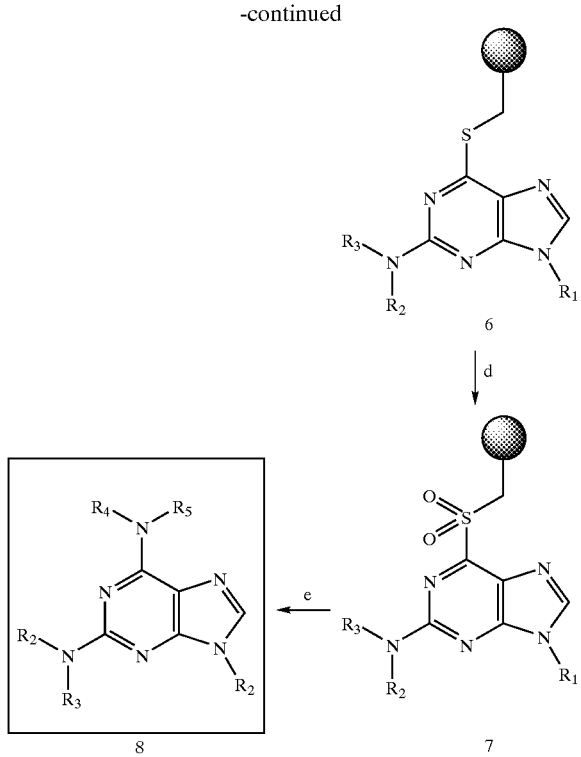

a). 1 5 equiv of $R_1OH$, 1.8 equiv of $PPh_3$, 1 3 equiv of DiAD, THF, RT,
b). 0.5 equiv of mercaptomethyl polystyrene resin, BuOH, 1 equiv of DiEA, 80° C.
c). 3 equiv of $R_2R_3NH$, 4 equiv of DiEA, BuOH, 80° C.
d). 10 equiv of m-CPBA/NaOH (1:1), dioxane
e). 0.9 equiv of $R_4R_5NH$, anhydrous 1,4-dioxane, 80° C.

Figure 2:
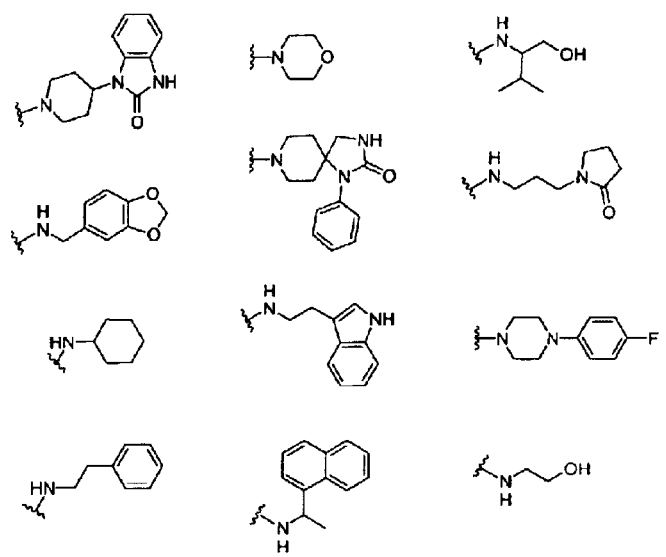
FIG. 2 shows validated substituents at the C2 position of purine introduced by nucleophilic aromatic substitution with primary and secondary amines as shown in Scheme 11.
Figure 3:
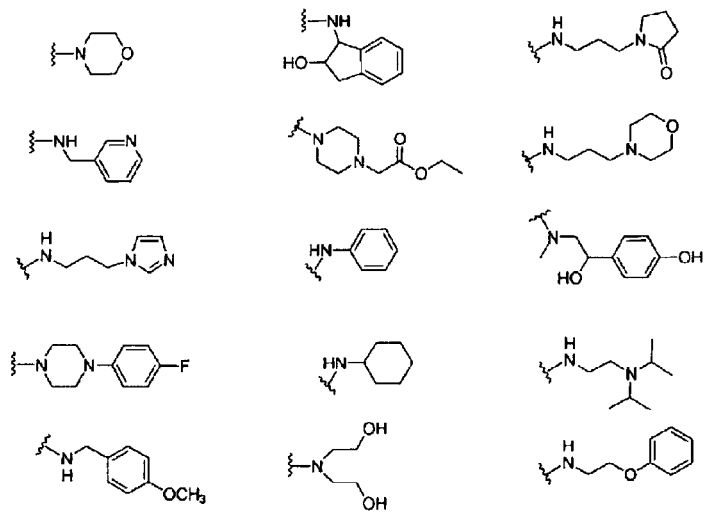
FIG. 3 shows validated substituents at the C6 position of purine introduced by nucleophilic aromatic substitution with primary and secondary amines as shown in Scheme 11.

The C2 position can be substituted with variety of primary amines, such as sterically hindered 2-amino-3-methyl-butanol, and cyclic/acyclic secondary amines (see, FIG. 2). Normally five equivalents of amines are used at a concentration of 2M in butanol to ensure quantitative substitution of 2-chloro-purine. Finally, the C6 displacement of the sulfonyl group can be carried out with diverse primary and secondary amines and electron-rich anilines (see, FIG. 3). Rather than use excess amine to quantitatively release resin-bound purine, which requires follow-up purification by solid supported liquid extraction (SLE) (Johnson et al, Tetrahedron Lett. 54: 4097 (1998)), a limited amount of amine (0.8 equivalent) can be used. This procedure essentially gave the pure purine product without the need of SLE purification. It should be noted that the final derivatization step should preferably be carried under anhydrous conditions, since water can also react with the sulfonyl purine to release guanine as a by-product.

Detailed reaction conditions useful in these methods are described in Example 2.

In summary, this aspect of the invention provides an alternative approach or method for making combinatorial 2,6,9-trisubstituted purine libraries by capturing an N9 substituted 2-fluoro-6-chloropurine at the C6 position via a thioether linkage and subsequently modifying the polymer-bound purine intermediate at the C2 position, followed by substitution at the C6 position with concomitant release.

Pharmaceutical Formulations

In another preferred embodiment, the present invention provides a pharmaceutical formulation comprising a compound of the invention and a pharmaceutically acceptable carrier.

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{+2}$ antagonists (e.g., verapamil, nifedipine, nitrendipine and caroverine); amphotericin; triparanol analogues (e.g., tamoxifen); anti-arrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired. to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

EXAMPLES

The following examples are offered to illustrate, but not to limit the present invention.

General

N9 Mitsunobu alkylation reactions and C6 sulfone displacement reactions are carried out under anhydrous conditions under argon atmosphere. C2 resin capture reactions are carried out in 4 mL scintillation glass vials unless otherwise noted. Anhydrous tetrahydrofuran, and 1,4-dioxane are obtained by passing them through commercially available alumina columns. All other reagents, resins, and solvents are purchased at highest commercial quality and used without further purification. Purity of compounds are assessed by reverse-phase liquid chromatography/mass spectrometer (Agilent Series 1100 LC-MS; elution method: starting from 5% to 95% acetonitrile in water with 0.5% acetic acid in 8 minutes and finishing at 10 minute with 95% acetonitrile using a Phenomenex Luna 50*2.00 mm 5$\mu$ C18 column) with an UV detector at $\lambda$=255 nm (reference at 360 nm) and an API-ES ionization source. NMR spectra are recorded on Bruker-400 MHz instrument and calibrated using residual undeuterated solvent as an internal reference. The following abbreviations are used to designate the multiplicities: s=singlet, d=doublet, t=triplet, q=quartet, m=multiplet.

Example 1

General Procedure for the Combinatorial Synthesis of 2,6,9-Trisubstituted Purines Reductive Amination for Synthesis of PAL-Resin-Bound Amine (1)

To a suspension of 4-formyl-3,5-dimethoxyphenoxymethyl functionalized polystyrene resin (PAL) (10.0 g, 11.3 mmol) in DMF (350 mL) is added a primary amine (56.5 mmol), followed by addition of sodium triacetoxyborohydride (7.18 g, 33.9 mmol) and acetic acid (6.52 mL, 113 mmol). The mixture is shaken gently at room temperature for 12 hours and then washed with methanol (300 mL×4) and dichloromethane (300 mL×4) and dried under vacuum. The complete conversion of PAL aldehyde to resin-bound amine is confirmed by disappearance of the aldehyde stretch.

2-Fluoro-6-phenylsulfenylpurine (2)

To a solution of 2-fluoro-6-chloropurine (10.0 g, 57.9 mmol) in methanol (200 mL) is added diisopropylethylamine (25.2 mL, 144.7 mmol). The mixture is cooled to 0° C. and followed by slow addition of thiophenol (11.9 mL, 115.8 mmol) via an addition funnel over one hour. The reaction is stirred at 0° C. for 12 hours. The solvent is then removed under reduced pressure and the solid is collected by filtration and washed twice with hexanes. The collected solid is further purified by re-crystallization from methanol to afford desired product (11.8 g, 83% yield). $^1$H NMR (400 MHz, (CD$_3$)$_2$SO) $\delta$ 7.54 (m, 3H), 7.66(m, 2H), 8.49(s, 1H); MS C$_{11}$H$_7$FN$_4$S [MH$^+$] 246.04, found: 247.05.

2-Fluoro-6-phenylsulfenyl-9-alkylpurine (3)

To a flame-dried round bottom flask (500 mL) was added 2-fluoro-6-phenylsulfenylpurine (10.0 g, 40.6 mmol), triphenylphosphine (19.2 g, 73.1 mmol) and alcohol (52.8 mmol), followed by dissolving them in THF (anhydrous, 350 mL). The solution was cooled down to −30° C. and diisopropyl azodicarboxylate (12.0 mL, 60.9 mmol) was added dropwise. The reaction was allowed to warm up to room temperature and stirred under argon. After overnight, the solvent was removed under reduced pressure and the crude material was directly used in the next step without further purification.

Resin Capture of 3 at C2 from Crude Mitsunobu Reaction (4)

To a solution of crude 2-fluoro-6-phenylsulfenyl-9-alkylpurine (0.15 mmol) in n-butanol (1.0 mL) is added PAL-resin-bound amine 1 (0.10 mmol), followed by addition of diisopropylethylamine (0.30 mmol). The suspension is heated to 80° C. under argon. After 12 hours, the resin is washed with methanol (3 mL×4) and dichloromethane (3 mL×4) and dried under vacuum. The complete conversion of secondary amine (PAL-amine) to tertiary amine is confirmed using the bromophenol blue test. ((a) Krchñák et. al., *Int. J. Petp. Protein Res.*, 32, 415–416 (1988); (b) Krchñák et. al., *Collect. Czech. Chem. Commun.*, 53, 2542–2548 (1988).)

Activation of C6 by Oxidation of Thioether to Sulfone (5)

To a solution of m-CPBA (0.23 g, 75%, 1.0 mmol) in 1,4-dioxane (9 mL) cooled to 0° C. is added NaOH (1 mL, 1M, 1.0 mmol) aqueous solution, followed by addition of resin 4 (0.10 mmol). The suspension is shaken gently at room temperature. After 8 hours the resin is washed with methanol (3 mL×4) and dichloromethane (3 mL×4) and dried under vacuum.

C6 Displacement with Amines (6) and Product Cleavage (7)

The resin 5 (0.05 mmol) is suspended in anhydrous 1,4-dioxane (0.6 mL), followed by addition of an amine (0.1 mmol). After overnight shaking at 80° C., the resin is washed with methanol (1 mL×4) and dichloromethane (1 mL×4) and dried under vacuum to afford resin 6. Resin 6 is subsequently cleaved using CH$_2$Cl$_2$:TFA:Me$_2$S:H$_2$O/ 45:45:5:5/v:v:v:v (0.5 mL) to afford desired product 7 (in average >85% HPLC purity, 80% purified yield).

Validation of Methods Using Various Substituents

The following Tables 3 through 5 provide retention times, and calculated and observed molecular weights for compounds having various substituents at the N9, C2, and C6 positions of purines. These results demonstrate that the methods of the invention are applicable for a wide variety of different substituents.

TABLE 3

Validation of N9 substituents.

| Entry | N9 substituent (R₂) | Retention Time (min)[1] | Calculated [M] | Observed [MH⁺] | HPLC purity (%) | Isolated yield (%) |
|---|---|---|---|---|---|---|
| 1 | (ethyl-pyrrolidinone) | 4.79 | 482.25 | 486.3 | 91 | 83 |
| 2 | (ethyl-piperidine) | 3.96 | 485.29 | 486.3 | 84 | 76 |
| 3 | (naphthylmethyl) | 7.09 | 514.25 | 515.2 | 86 | 81 |
| 4 | —CH₃ | 4.88 | 388.20 | 389.2 | 93 | 86 |
| 5 | (benzyl) | 6.31 | 464.23 | 465.2 | 90 | 85 |
| 6 | (ethyl-morpholine) | 3.92 | 487.27 | 488.3 | 85 | 80 |
| 7 | (propyl-NH₂) [a] | 2.96 | 417.23 | 418.2 | 86 | 79 |
| 8 | (ethyl-COOH) [b] | 3.77 | 432.19 | 433.2 | 89 | 77 |
| 9 | —H [c] | 4.65 | 374.19 | 375.2 | 86 | 79 |

TABLE 3-continued

Validation of N9 substituents.

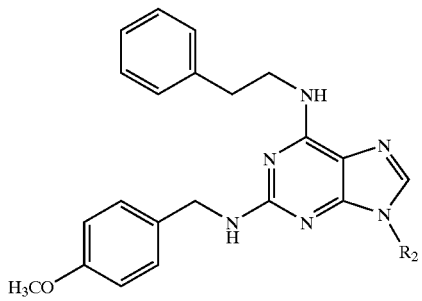

| Entry | N9 substituent ($R_2$) | Retention Time (min)[1] | Calculated [M] | Observed [MH$^+$] | HPLC purity (%) | Isolated yield (%) |
|---|---|---|---|---|---|---|

[a]Mitsunobu alkylation with t-Butyl N-(2-hydroxyethyl)-carbamate.
[b]Alkylation with t-Butyl-bromoacetate (2 equiv) in the presence of $K_2CO_3$ (3 equiv) in DMF at RT.
[c]N9 protected with THP.
[a,b,c]For these three entries, the protecting groups were all removed during final TFA cleavage.
[1]16 minutes elution method was used, except for entry 9 which 10 minutes elution method was used.

TABLE 4

Validation of C2 substituents.

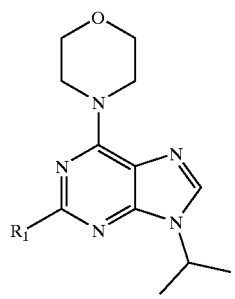

| Entry | C2 substituent ($R_1$) | Retention Time (min)[2] | Calculated [M] | Observed [MH$^+$] | HPLC purity (%) | isolated yield (%) |
|---|---|---|---|---|---|---|
| 1 | –NH–C$_6$H$_4$–Cl (4-chlorobenzylamino) | 4.87 | 386.16 | 387.2 | 92 | 85 |
| 2 | HN–cyclohexyl | 5.62 | 344.23 | 345.2 | 88 | 78 |
| 3 | HN–CH$_2$CH$_2$–OH | 2.93 | 306.18 | 307.20 | 87 | 80 |
| 4 | –NH–CH$_2$–C$_6$H$_4$–OCH$_3$ | 4.42 | 382.21 | 383.3 | 93 | 84 |

TABLE 4-continued
Validation of C2 substituents.
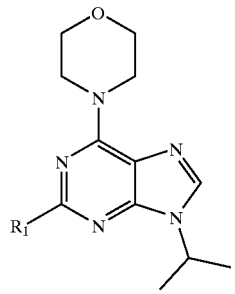
| Entry | C2 substituent (R₁) | Retention Time (min)[2] | Calculated [M] | Observed [MH⁺] | HPLC purity (%) | isolated yield (%) |
|---|---|---|---|---|---|---|
| 5 | —NH–(CH₂)₃–pyrrolidinone | 3.33 | 387.24 | 388.3 | 90 | 82 |
| 6 | —NH–CH(CH₃)–naphthyl | 5.07 | 416.23 | 417.2 | 83 | 77 |
| 7 | —NH–CH₂–(benzo[d][1,3]dioxol-5-yl) | 4.38 | 396.19 | 397.2 | 91 | 85 |
| 8 | —NH–(CH₂)₂–(1H-indol-3-yl) | 4.12 | 405.23 | 406.3 | 86 | 80 |
| 9 | —NH–CH(iPr)–CH₂OH | 3.63 | 348.23 | 349.3 | 85 | 80 |
[2]10 minutes elution method was used.

TABLE 5

Validation of C6 substituents.

[Structure: 2-(phenethylamino)-9-isopropyl-6-R₃-purine]

| Entry | C6 substituent (R₃) | Retention Time (min)[3] | Calculated [M] | Observed [MH⁺] | HPLC purity (%) | Isolated yield (%) |
|---|---|---|---|---|---|---|
| 1 | piperazinyl-(4-fluorophenyl) | 5.11 | 459.25 | 460.3 | 91 | 85 |
| 2 | NH-CH₂-(3-pyridyl) | 3.52 | 387.22 | 388.2 | 86 | 79 |
| 3 | NH-(CH₂)₃-imidazolyl | 3.01 | 404.24 | 405.3 | 85 | 80 |
| 4 | NH-(2-hydroxyindanyl) | 4.27 | 428.23 | 429.2 | 86 | 80 |
| 5 | piperazinyl-CH₂-C(O)-O-Et | 3.86 | 451.27 | 452.3 | 90 | 83 |
| 6 | HN-phenyl | 7.05[1] | 372.21 | 373.2 | 83 | 75 |
| 7 | NH-(CH₂)₃-(2-oxopyrrolidinyl) | 3.70 | 421.26 | 422.3 | 89 | 81 |
| 8 | NH-CH₂CH₂-N(iPr)₂ | 3.44 | 423.31 | 424.3 | 88 | 82 |
| 9 | NH-CH₂-(4-methoxyphenyl) | 4.54 | 416.23 | 417.20 | 90 | 84 |

[3] 10 minutes elution method was used.

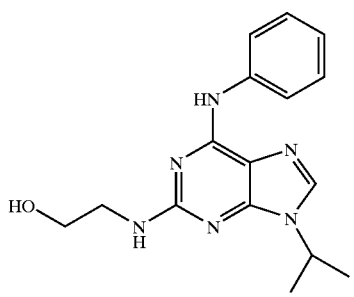

1H NMR (400 MHz, CDCl$_3$) δ: 1.52 (d, 6H, 6.8 Hz), 3.59–3.63 (m, 2H), 3.84–3.87 (m, 2H), 4.57–4.65 (m, 1H), 5.51–5.53 (m, 1H), 7.03–7.07 (m, 1H), 7.27–7.33 (m, 2H), 7.59 (s, 1H), 7.75–7.77 (m, 2H), 8.16 (s, 1H); HRMS calc'd for [MH$^+$] C$_{16}$H$_{21}$N$_6$O 313.1777, found: 313.1778.

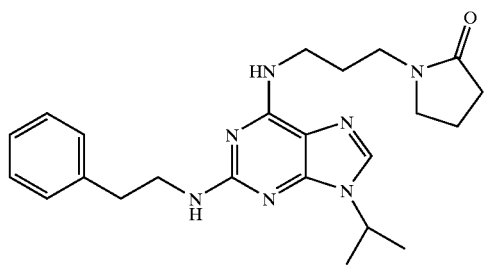

1H NMR (400 MHz, CDCl$_3$) δ: 1.54 (d, 6H, 6.8 Hz), 1.94 (m, 4H), 2.39 (m, 2H), 2.94 (t, 2H, J=7.3 Hz), 3.41–3.49 (m, 8H), 3.66 (br, 2H), 4.67 (m, 1H, 6.8 Hz), 7.23 (m, 3H), 7.31 (m, 2H), 7.62 (s, 1H); MS (ES) calc'd for [MH$^+$] C$_{23}$H$_{32}$N$_7$O 422.27, found 422.30.

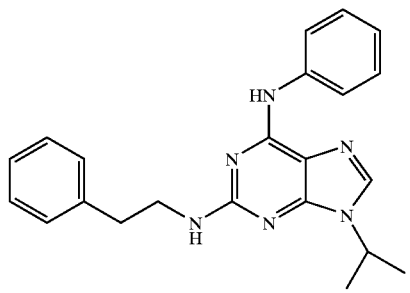

1H NMR (400 MHz, CDCl$_3$) δ: 1.57 (d, 6H, J=6.8 Hz), 2.96 (t, 2H, J=7.6 Hz), 3.73 (m, 2H), 4.68 (m, 1H), 5.02 (br, 1H), 4.67 (m, 1H, J=6.8 Hz), 7.05 (m, 1H), 7.21–7.34 (m, 6H), 7.58 (s, 1H), 7.79 (m, 2H); MS (ES) calc'd for [MH$^+$] C$_{22}$H$_{25}$N$_6$ 373.21, found 373.20.

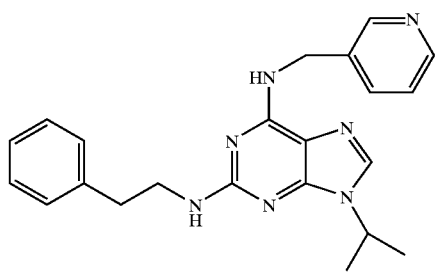

1H NMR (400 MHz, CDCl$_3$) δ: 1.55 (d, 6H, J=6.8 Hz), 2.90 (t, 2H, J=7.2 Hz), 3.65 (m, 2H), 4.65 (m, 1H, J=6.8 Hz), 4.81 (d, 2H, J=5.1 Hz), 4.87 (br, 1H), 6.06 (br, 1H), 7.05 (m, 1H), 7.21–7.31 (m, 6H), 7.50 (s, 1H), 7.69 (m, 1H), 8.50 (dd, 1H, J=1.3 Hz), 8.64 (d, 1H, J=1.5 Hz); MS (ES) calc'd for [MH$^+$] C$_{22}$H$_{26}$N$_7$ 388.22, found: 388.20.

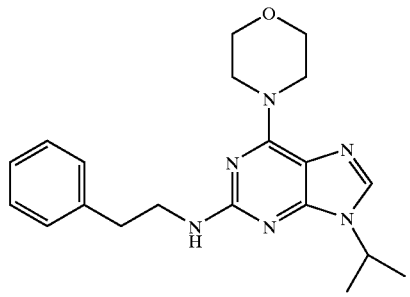

1H NMR (400 MHz, CDCl$_3$) δ: 1.57 (d, 6H, J=6.8 Hz), 2.97 (t, 2H, J=7.1 Hz), 3.66 (t, 2H, J=7.3 Hz), 3.81 (t, 4H, J=4.8 Hz), 4.25 (br, 4H), 4.75 (m, 1H, J=6.8 Hz), 7.28 (m, 3H), 7.34 (m, 2H), 7.56 (s, 1H); MS (ES) calc'd for [MH$^+$] C$_{20}$H$_{27}$N$_6$O 367.22, found 367.20.

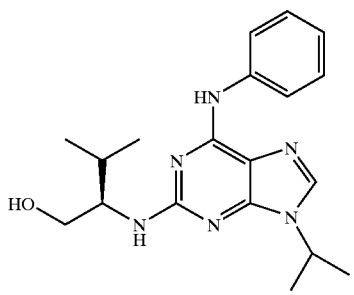

1H NMR (400 MHz, CDCl$_3$) δ:1.03 (d, 3H, J=6.8 Hz), 1.05 (d, 3H, J=6.8 Hz), 1.98–2.03 (m, 1H), 1.52 (d, 3H, J=6.8 Hz), 1.54 (d, 3H, J=6.8 Hz), 2.01 (m, 1H), 3.71–3.76 (m, 1H), 3.89–3.92 (m, 2H), 4.57 (sept., 1H, 6.8 Hz), 5.03 (br, 1H), 7.07 (t, 1H, J=8.8 Hz), 7.39 (br, 1H), 7.57 (s, 1H), 7.89 (s, 1H), 8.02 (br, 1H); MS (ES) calc'd for C$_{19}$H$_{27}$N$_6$O [MH$^+$] 355.22, found: 355.20.

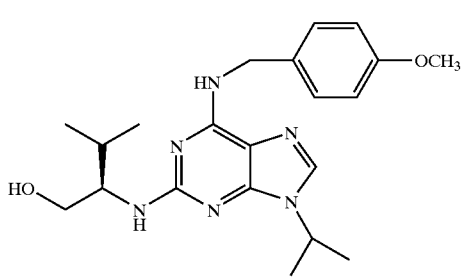

1H NMR (500 MHz, d6-DMSO) δ: d 0.85 (d, 6H, 7.1 Hz), 1.44 (d, 6H, 7.1 Hz), 1.93 (m, 1H), 3.31 (s, 2H), 3.46 (d, 2H, 5.3 Hz), 3.69 (s, 3H), 3.79 (m, 1H), 4.49 (m, 3H), 5.75 (s, 1H), 6.83 (d, 2H, J=8.7), 7.27 (d, 2H, J=8.7), 7.75 (s, 1H); HRMS calc'd for C$_{21}$H$_{30}$H$_6$O$_2$ · [MH$^+$] 399.2508, found: 399.2510.

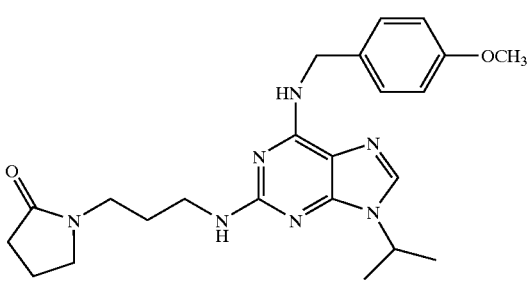

1H NMR (400 MHz, CDCl$_3$) δ: 1.61 (d, 6H, J=6.8 Hz), 1.92 (m, 2H), 2.10 (m, 2H), 2.52 (t, 2H, J=6.3 Hz), 3.44–3.56 (m, 6H), 3.80 (s, 3H), 4.81 (b, 3H)), 6.88 (d, 2H, J=7.9 Hz), 7.32 (d, 2H), 8.08 (s, 1H); MS (ES) calc'd for [MH$^+$] C$_{23}$H$_{32}$N$_7$O$_2$ 438.26, found 438.30

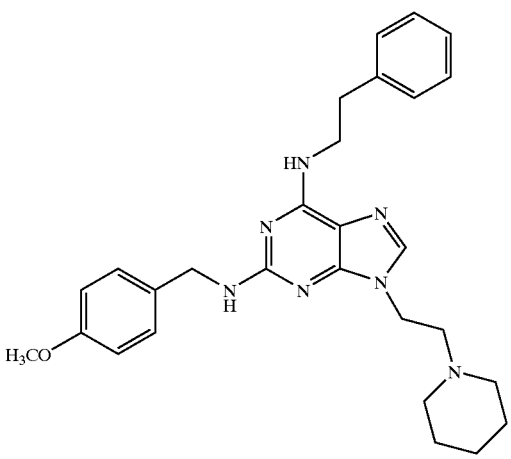

1H NMR (400 MHz, CDCl$_3$) δ: 1.44 (m, 2H), 1.56 (m, 4H), 2.45 (m, 4H), 2.65 (t, 2H, J=13.5 Hz), 2.94 (t, 2H, J=7.1 Hz), 3.78 (s, 3H), 3.84 (m, 2H), 4.14 (t, 2H), J=13.6 Hz), 4.57 (d, 2H, J=5.8 Hz), 6.85 (d, 2H, J=8.7 Hz), 7.21–7.32 (m, 7H), 7.57 (s, 1H); MS (ES) calc'd for [MH$^+$] C$_{28}$H$_{36}$N$_7$O 486.30, found: 486.30.

Example 2

A Resin-Capture-Release Strategy Towards Combinatorial Libraries of 2,6,9-Substituted Purines General. Purity of compounds were assessed by reverse-phase liquid chromatography—mass spectrometer (Agilent Series 1100 LC-MS) with an UV detector at λ=255 nm (reference at 360 nm) and an API-ES ionization source. NMR spectra were recorded on Bruker-400 MHz and 500 MHz instrument and calibrated using residual undeuterated solvent as an internal reference. The following abbreviations were used to designate the multiplicities: s=singlet, d=doublet, t=triplet, q=quartet, m=multiplet. LC elution methods (using a Phenomenex Luna 50*2.00 mm 5μ C18 column): (1) 10 minutes method: starting from 5% solvent A (acetonitrile) in solvent B (water with 0.5% acetic acid) and running the gradient to 95% A in 8 minutes, followed by 2 minutes elution with 95% A. (2) 6 minutes method: starting from 5% solvent A (acetonitrile) in solvent B (water with 0.5% acetic acid) and running the gradient to 95% A in 5 minutes, followed by 1 minutes elution with 95% A.

Representative Experimental Procedures:

2-Phenylsulfenylhypoxanthine (2). To a solution of 2-bromohypoxanthine (10.0 g, 46.5 mmol) in methanol (200 mL) was added thiophenol (9.55 mL, 93.0 mmol) and diisopropylethylamine (20.2 mL, 116.3 mmol). The reaction was stirred at 90° C. for overnight. The solvent was removed under reduced pressure and the solid was collected by filtration and washed with hexanes (100 mL×2). The collected solid was further purified by re-crystallization from methanol to afford desired product (10.1 g, 89% yield). $^1$H NMR (400 MHz, (CD$_3$)$_2$SO) δ 7.50(m, 3H), 7.62 (m, 2H), 7.97 (s, 1H); MS (ES) calc'd for C$_{11}$H$_8$N$_4$OS [MH$^+$] 245.05, found: 245.05.

2-Phenylsulfenyl-6-chloro-purine (3). To a flame-dried round bottom flask (200 mL) was added 2-Phenylsulfenylhypoxanthine 2 (1.22 g, 5.0 mmol), tetrabutyl-ammonium chloride (anhydrous, 2.78 g, 10.0 mmol) and N,N-dimethylaniline (0.63 mL, 5.0 mmol), followed by dissolving them in acetonitrile (anhydrous, 50 mL). To the solution phosphorus oxychloride (2.8 mL, 30.0 mmol) was added dropwise. The reaction was refluxed under argon. After 2 hours, the reaction was cooled to 0° C. on an ice bath and quenched by addition of saturated sodium bicarbonate solution. The aqueous layer was extracted with ethyl acetate (4×100 mL). The combined organic layers were dried over sodium sulfate, and were concentrated on the rotary evaporator. The crude product was further purified by re-crystallization from methanol to afford desired product 3 as white solid (0.94 g, 72%). $^1$H NMR (400 MHz, (CD$_3$)$_2$SO) 7.50 (m, 3H), δ 7.65 (m, 2H), 8.53 (s, 1H); MS (ES) calculated for C$_{11}$H$_7$ClN$_4$S [MH$^+$] 263.02, found: 263.00.

Solution phase N9 Mitsunobu Alkylation of Purine (4). To a flame-dried round bottom flask (500 mL) was added 2-fluoro-6-chloro-purine (7.0 g, 40.6 mmol), triphenylphosphine (19.2 g, 73.1 mmol) and alcohol (52.8 mmol), followed by dissolving them in THF (anhydrous, 350 mL). The solution was cooled down to −30° C. and diisopropyl azodicarboxylate (12.0 mL, 60.9 mmol) was added dropwise. The reaction was allowed to warm up to room temperature and stirred under argon. After overnight, the solvent was removed under reduced pressure and the crude material was directly used in the next step without further purification.

Resin Capture of N9-alkylated Purine Scaffold at C6 (5). To a solution of crude 2-fluoro-6-chloro-9-alkylpurine (15.0 mmol) in n-butanol (200 mL) was added mercaptomethyl polystyrene resin (10.0 mmol, Midwest Biotech), followed by addition of diisopropylethylamine (5.2 mL, 30.0 mmol). The suspension was heated to 80° C. under argon. After overnight, the resin was washed by methanol (200 mL×4) and dichloromethane (200 mL×4) and dried under vacuum.

C2 Amination of Captured Purine (6). The resin 5 (0.10 mmol) was suspended in n-butanol (1.0 mL), followed by addition of an amine (0.30 mmol) and diisopropylethylamine (0.40 mmol). After overnight shaking at 80° C., the resin was washed by methanol (3 mL×4) and dichloromethane (3 mL×4) and dried under vacuum.

Activation of C6 by Oxidizing Sulfenyl Group to Sulfonyl Group (7). To a solution of m-CPBA (0.23 g, 75%, 1.0 mmol) in 1,4-dioxane (9 mL) cooled to 0° C. was added NaOH (1 mL, 1M, 1.0 mmol) aqueous solution, followed by addition of resin 4 (0.10 mmol). The suspension was shaken gently at room temperature. After 8 hours the resin was washed by methanol (3 mL×4) and dichloromethane (3 mL×4) and dried under vacuum.

C6 Displacement with Amines and Product Releasing (8). The resin 7 (0.05 mmol) was suspended in anhydrous 1,4-dioxane (0.6 mL), followed by addition of an amine (0.1 mmol). After overnight shaking at 80° C., the resin was filtered using a polypropylene cartridge (45μ PTFE frit) and the flow-through solution was collected. The resin was subsequently washed by dichloromethane (0.5 mL×3) and flow-through was combined and solvent was removed under reduced pressure to afford desired product 8 (in average >85% HPLC purity, 80% purified yield).

The following Tables 6 and 7 show experimental data obtained for compounds prepared using the methods of the invention and having various substituents at the C2 and C6 positions. These results demonstrate the wide applicability of the methods of the invention.

TABLE 6

Validation of C2 substituents.

| Entry | N9 substituent ($R_2$) | Retention Time (min) | Calculated [M] | Observed [MH$^+$] | HPLC purity (%) | Isolated yield[2] (%) |
|---|---|---|---|---|---|---|
| 1 | (piperidinyl-benzimidazolone) | 4.57 | 462.25 | 463.3 | 90 | 81 |
| 2 | (benzodioxole methylamino) | 4.38 | 396.19 | 397.2 | 91 | 86 |
| 3 | (cyclohexylamino) | 5.62[1] | 344.23 | 345.2 | 87 | 81 |
| 4 | (phenethylamino) | 5.78[1] | 366.22 | 367.3 | 90 | 82 |
| 5 | (morpholino) | 5.30[1] | 332.20 | 333.2 | 94 | 87 |
| 6 | (phenyl-diazaspiro) | 4.63 | 476.26 | 477.3 | 84 | 79 |

TABLE 6-continued
Validation of C2 substituents.
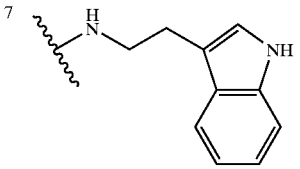
| Entry | N9 substituent (R₂) | Retention Time (min) | Calculated [M] | Observed [MH⁺] | HPLC purity (%) | Isolated yield[2] (%) |
|---|---|---|---|---|---|---|
| 7 | 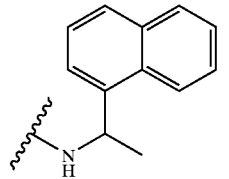 | 4.12 | 405.23 | 406.3 | 84 | 77 |
| 8 | 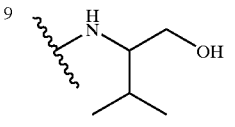 | 5.07 | 416.23 | 417.3 | 85 | 80 |
| 9 | 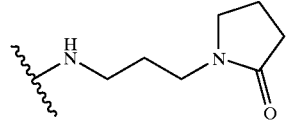 | 3.63 | 348.23 | 349.3 | 83 | 79 |
| 10 | 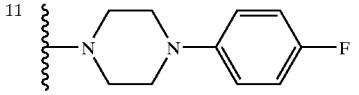 | 3.33 | 387.24 | 388.3 | 86 | 82 |
| 11 | 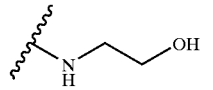 | 5.22 | 425.23 | 426.2 | 89 | 83 |
| 12 |  | 2.93 | 306.18 | 307.2 | 90 | 84 |
[1] 10 minutes elution method was used. For other entries, 6 minutes elution method was used.
[2] Isolated yields are based on the amount of amine (0.8 equiv) used for the final displacement releasing.

TABLE 7
Validation of C6 substituents.
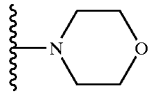
| Entry | C6 substituent (NR₄R₅) | Retention Time (min) | Calculated [M] | Observed [MH⁺] | HPLC purity (%) | Isolated yield[2] (%) |
|---|---|---|---|---|---|---|
| 1 | 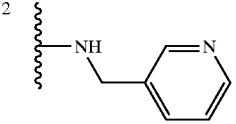 | 5.63[1] | 366.22 | 367.2 | 91 | 83 |
| 2 | 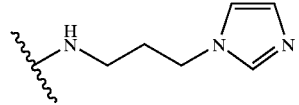 | 3.52 | 387.22 | 388.2 | 84 | 77 |
| 3 | 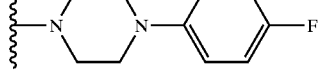 | 3.01 | 404.24 | 405.3 | 88 | 82 |
| 4 | 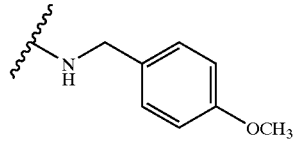 | 5.11 | 459.25 | 460.3 | 91 | 86 |
| 5 | 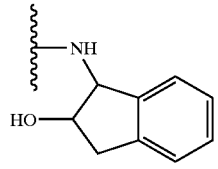 | 4.54 | 416.23 | 417.20 | 90 | 84 |
| 6 | 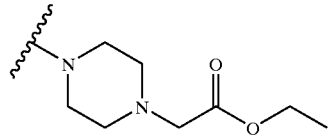 | 4.27 | 428.23 | 429.2 | 82 | 77 |
| 7 | 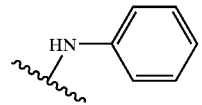 | 3.86 | 451.27 | 452.3 | 87 | 81 |
| 8 |  | 7.05[1] | 372.21 | 373.2 | 86 | 80 |

TABLE 7-continued

Validation of C6 substituents.

| Entry | C6 substituent (NR₄R₅) | Retention Time (min) | Calculated [M] | Observed [MH⁺] | HPLC purity (%) | Isolated yield[2] (%) |
|---|---|---|---|---|---|---|
| 9 | HN-cyclohexyl | 5.73[1] | 378.25 | 379.3 | 87 | 81 |
| 10 | N(CH₂CH₂OH)₂ | 3.47 | 384.23 | 385.3 | 84 | 76 |
| 11 | NH-(CH₂)₃-pyrrolidinone | 3.70 | 421.26 | 422.3 | 88 | 83 |
| 12 | NH-(CH₂)₃-morpholine | 3.04 | 423.27 | 424.3 | 89 | 82 |
| 13 | N(CH₃)CH₂CH(OH)-C₆H₄-OH | 3.87 | 446.24 | 447.3 | 84 | 76 |
| 14 | NH-CH₂CH₂-N(iPr)₂ | 3.44 | 423.31 | 424.3 | 87 | 81 |
| 15 | NH-CH₂CH₂-O-C₆H₅ | 4.60 | 416.23 | 416.2 | 92 | 84 |

[1]10 minutes elution method was used. For other entries, 6 minutes elution method was used.
[2]Isolated yields are based on the amount of amine (0.8 equiv) used for the final displacement releasing.

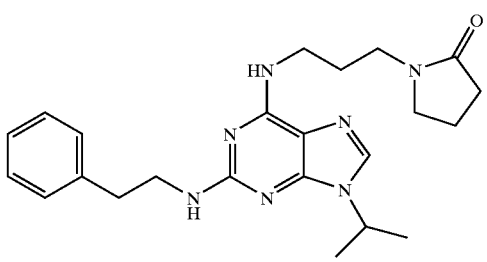

1H NMR (400 MHz, CDCl₃) δ: 1.54 (d, 6H, 6.8 Hz), 1.94 (m, 4H), 2.39 (m, 2H) 2.94 (t, 2H, J=7.3 Hz), 3.41–3.49 (m, 8H), 3.66 (br, 2H), 4.67 (m, 1H, 6.8 Hz), 7.23(m, 3H), 7.31 (m, 2H), 7.62 (s, 1H); MS (ES) calc'd for [MH⁺] $C_{23}H_{32}N_7O$ 422.27, found 422.30.

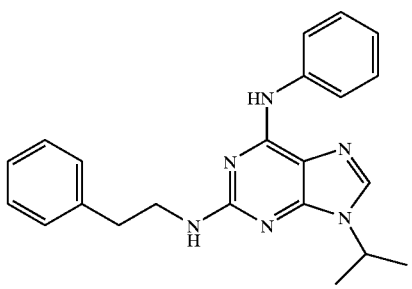

1H NMR (400 MHz, CDCl₃) δ: 1.57 (d, 6H, J=6.8 Hz), 2.96 (t, 2H, J=7.6 Hz), 3.73 (m, 2H), 4.68 (m, 1H), 5.02 (br, 1H), 4.67 (m, 1H, J=6.8 Hz), 7.05 (m, 1H), 7.21–7.34 (m, 6H), 7.58 (s, 1H), 7.79 (m, 2H); MS (ES) calc'd for [MH⁺] $C_{22}H_{25}N_6$ 373.21, found 373.20.

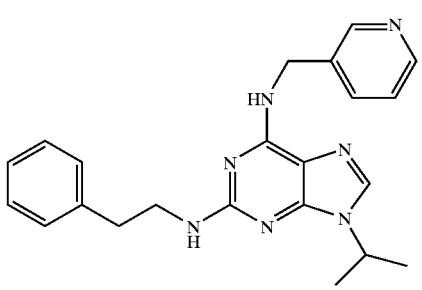

1H NMR (400 MHz, CDCl₃) δ: 1.55 (d, 6H, J=6.8 Hz), 2.90 (t, 2H, J=7.2 Hz), 3.65 (m, 2H), 4.65 (m, 1H, J=6.8 Hz), 4.81 (d, 2H, J=5.1 Hz), 4.87 (br, 1H), 6.06 (br,1H), 7.05 (m, 1H), 7.21–7.31 (m, 6H), 7.50 (s, 1H), 7.69 (m, 1H), 8.50 (dd, 1H, J=1.3 Hz), 8.64 (d, 1H, J=1.5 Hz); MS calc'd for [MH⁺] $C_{22}H_{26}N_7$ 388.22, found: 388.20.

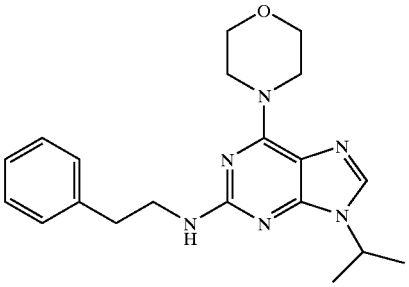

1H NMR (400 MHz, CDCl₃) δ: 1.57 (d, 6H, J=6.8 Hz), 2.97 (t, 2H, J=7.1 Hz), 3.66 (t, 2H, J=7.3 Hz), 3.81 (t, 4H, J=4.8 Hz), 4.25 (br, 4H), 4.75 (m, 1H, J=6.8 Hz), 7.28 (m, 3H), 7.34 (m, 2H), 7.56 (s, 1H); MS (ES) calc'd for [MH⁺] $C_{20}H_{27}N_6O$ 367.22, found 367.20.

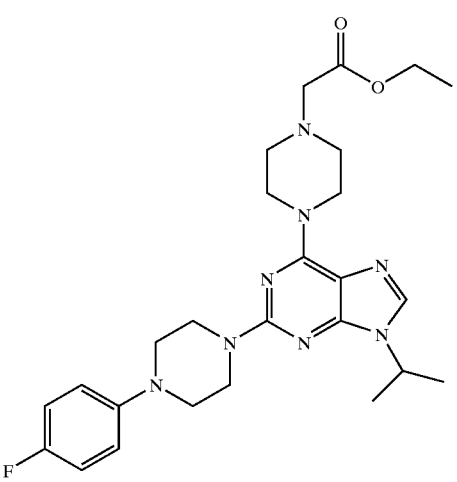

1H NMR (400 MHz, CDCl₃) δ: 1.30 (t, 3H, J=7.1 Hz), 1.59 (d, 6H, J=6.8 Hz), 3.52(m, 8H), 3.94 (s, 2H), 4.20 (t, 4H, J=4.5 Hz), 4.27 (q, 2H, J=7.1 Hz), 4.41 (br, 4H), 4.80 (m, 1H, J=6.8 Hz), 7.16 (d, 2H, J=9.1 Hz), 7.41 (d, 2H, J=9.1 Hz), 8.11 (s, 1H); MS (ES) calc'd for [MH⁺] $C_{26}H_{36}FN_8O_2$ 511.29, found: 511.30.

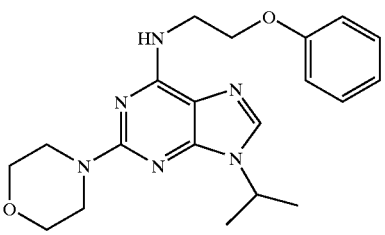

1H NMR (400 MHz, CDCl₃) δ: 1.58 (d, 6H, J=6.8 Hz), 3.76 (m, 8H), 4.02 (br, 2H), 4.20 (t, 2H, J=5.9 Hz), 4.75 (m, 1H, J=6.8 Hz), 6.93 (m, 3H), 7.26 (m, 2H), 7.84 (s, 1H); MS (ES) calc'd for [MH⁺] $C_{20}H_{27}N_6O_2$, 383.22, found: 383.20.

Example 3

Concise, Traceless Approaches Toward Combinatorial 2,9-Disubstituted Guanines and O6-Aryl-, O6-Alkyl-Purines Table 8 shows the retention times, as well as calculated and observed molecular weights for purines having various substituents at the C6 and C2 positions that were made using the methods of the invention. These results demonstrate that the methods are applicable to attachment of a wide variety of substituents to purine scaffolds.

TABLE 8

[Structure: 9-isopropyl-2-R₂-1H-purin-6(9H)-one scaffold with R₂ at C2 position]

| C6 subsitutuent (R₂) | | Retention Time (min) | Calculated [M] | Observed [MH⁺] |
|---|---|---|---|---|
| [2-chlorobenzylamino] | | 5.40 | 317.10 | 318.10 |
| [naphthalen-1-ylmethylamino] | | 4.41 | 333.16 | 334.20 |
| [2-hydroxyethylamino] | | 2.44 | 237.10 | 238.10 |
| [cyclohexylamino] | | 5.29 | 275.17 | 276.20 |
| [4-methoxybenzylamino] | | 4.84 | 313.15 | 314.20 |
| [pyridin-3-ylmethylamino] | | 0.50 | 284.14 | 285.20 |
| [4-methoxyphenyl] | a | 5.40 | 317.10 | 318.10 |
| [4-methoxyphenylamino] | a, b | 5.40 | 317.10 | 318.10 |
| [4-methoxyphenoxy] | a, b | 5.40 | 317.10 | 318.10 |

TABLE 8-continued

[Structure: purine core with OR at C6, X at C2, Y on N9]

| C2 subsitutuent (OR) | Retention Time (min) | Calculated [M] | Observed [MH+] |
|---|---|---|---|
| 4-iodo-2-methylphenoxy | 8.54 / 6.45 | 575.12 / 487.05 | 576.10 / 488.05 |
| 3-(trifluoromethoxy)phenoxy | 8.35 / 6.37 | 519.19 / 431.12 | 520.20 / 432.10 |
| 4-cyclopentylphenoxy | 8.99 / 6.94 | 503.27 / 415.20 | 504.30 / 416.20 |
| 7-methoxynaphthalen-2-yloxy | 8.17 / 6.14 | 515.23 / 427.16 | 516.20 / 428.20 |
| 4-methoxyphenoxy | 7.41 / 5.47 | 465.22 / 377.15 | 466.25 / 378.20 |
| 5-isopropyl-2-methylphenoxy | 8.70 / 6.61 | 491.27 / 403.20 | 492.30 / 404.20 |
| 3-biphenyloxy | 8.49 / 6.49 | 511.24 / 423.17 | 512.25 / 424.20 |
| 2,3-dihydro-1H-inden-5-yloxy | 8.39 / 6.23 | 475.24 / 387.17 | 476.20 / 388.20 |
| naphthalen-1-yloxy | 8.16 / 6.04 | 485.22 / 397.15 | 486.20 / 398.15 |

TABLE 8-continued

| Structure | | | |
|---|---|---|---|
| 4-hexyloxyphenoxy | 9.25 / 7.38 | 535.29 / 447.23 | 536.30 / 448.20 |
| 3,5-dimethylphenoxy | 8.28 / 6.12 | 463.24 / 375.17 | 464.25 / 376.20 |
| 2,6-difluorophenoxy | 7.83 / 5.75 | 471.19 / 383.12 | 472.20 / 384.10 |
| 2-methylphenoxy | 7.94 / 5.73 | 449.22 / 361.15 | 450.20 / 362.20 |
| 4-chlorophenoxy | 8.15 / 6.06 | 469.17 / 381.10 | 470.20 / 382.10 |

[1] X = phenethylamino, Y = phenethyl
[2] X = 4-methoxybenzylamino, Y = H

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of preparing a 2,6,9-substituted purine compound having the Formula I:

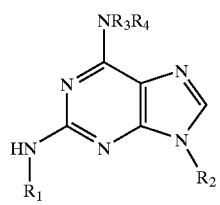

I wherein:
  $R_1$ and $R_2$ are independently selected from the group consisting of alkyl, substituted alkyl, cycloalkyl, aryl, substituted aryl, arylalkyl, substituted arylalkyl and heterocyclyl;
  $R_3$ is hydrogen and $R_4$ is selected from the group consisting of alkyl, substituted alkyl, cycloalkyl, aryl, substituted aryl, arylalkyl, substituted arylalkyl and heterocyclyl or $R_3$ and $R_4$ when taken together with the nitrogen and carbon atoms to which they are respectively attached form an optionally substituted saturated heterocyclic ring; the method comprising:

a) oxidizing a resin-bound compound of Formula II

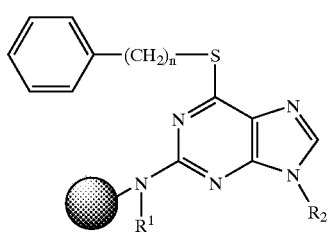

II wherein: $R_1$ and $R_2$ are as defined above and n is 0 or 1; to provide a resin-bound compound of Formula III

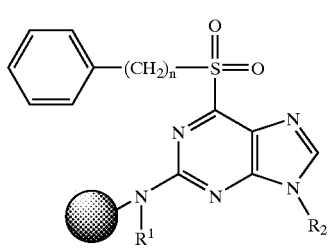

III wherein $R_1$, $R_2$ and n are as defined above;

b) reacting the compound of Formula III with an amine of Formula IV $NR_3R_4$

IV wherein $R_3$ and $R_4$ as defined above, to provide a resin-bound compound of Formula V

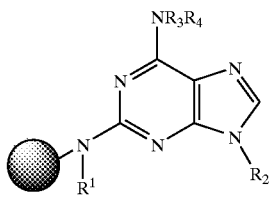

V wherein $R_1$, $R_2$, $R_3$ and $R_4$ are as defined above; and c) cleaving the resin-bound compound of Formula V from the resin to provide the substituted purine compounds of Formula I.

2. The method of claim 1, wherein the compound of Formula II is prepared by a) alkylating a compound of Formula VI

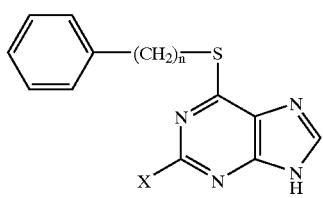

VI wherein X is fluoro, chloro or bromo and n is as defined above, to provide a compound of Formula VII

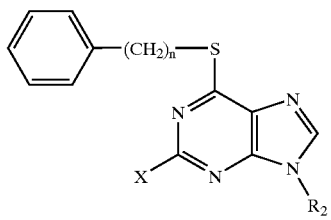

VII wherein $R_2$, X and n are as defined above; and b) capturing the compound of Formula VII with a resin-bound amine to provide the resin-bound compound of Formula II; or a) capturing a compound of Formula VI

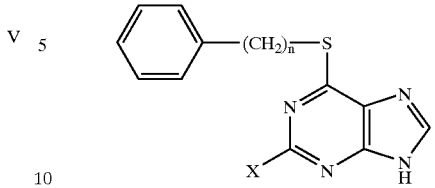

VI wherein X and n are as defined above, with a resin-bound amine to provide a resin-bound compound of Formula VIII

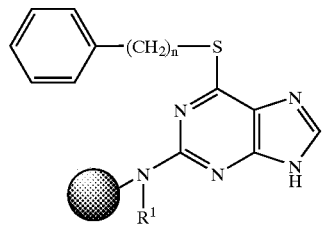

VIII wherein $R_1$ and n are as defined above; and b) alkylating the resin-bound compound of Formula VIII to provide the resin-bound compound of Formula II.

3. The method of claim 2, wherein the compound of Formula VI is prepared by reacting 2-halo-6-chloro-purine with a compound of Formula IX:

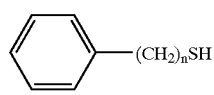

IX wherein n is as defined above, to provide the compound of Formula VI.

4. The method of claim 3, wherein the halo is fluoro, chloro or bromo.

5. The method of claim 1, wherein step (a) is carried out with m-chloroperbenzoic acid in a buffered solution.

6. The method of claim 1, wherein step (c) is carried out in the presence of trifluoroacetic acid.

7. The method of claim 2, wherein alkylating of the compound of Formula VI is carried out in the presence of an inert solvent and a tertiary phosphine.

8. The method of claim 1, wherein the resin is 4-formyl-3,5-dimethyloxyphenoxymethyl functionalized polystyrene resin.

* * * * *